United States Patent
Narayanan et al.

(10) Patent No.: US 9,260,746 B2
(45) Date of Patent: Feb. 16, 2016

(54) PHOTOINDUCED ELECTRON TRANSFER (PET) PRIMER FOR NUCLEIC ACID AMPLIFICATION

(75) Inventors: Jothikumar Narayanan, Atlanta, GA (US); Vincent Hill, Decatur, GA (US)

(73) Assignee: The United States of America as Represented by the Secretary of the Department of Health and Human Services, Centers for Disease Control and Prevention, Washington, DC (US)

( * ) Notice: Subject to any disclaimer, the term of this patent is extended or adjusted under 35 U.S.C. 154(b) by 775 days.

(21) Appl. No.: 12/743,607

(22) PCT Filed: Nov. 21, 2008

(86) PCT No.: PCT/US2008/084347
§ 371 (c)(1),
(2), (4) Date: May 19, 2010

(87) PCT Pub. No.: WO2009/067664
PCT Pub. Date: May 28, 2009

(65) Prior Publication Data
US 2011/0020804 A1   Jan. 27, 2011

Related U.S. Application Data

(60) Provisional application No. 60/989,768, filed on Nov. 21, 2007.

(51) Int. Cl.
C12P 19/34 (2006.01)
C12Q 1/68 (2006.01)

(52) U.S. Cl.
CPC ............ *C12Q 1/6818* (2013.01); *C12Q 1/6827* (2013.01); *C12Q 1/6844* (2013.01); *C12Q 1/6876* (2013.01)

(58) Field of Classification Search
None
See application file for complete search history.

(56) References Cited

U.S. PATENT DOCUMENTS

2002/0142309 A1* 10/2002 Dattagupta ................ 435/6
2006/0105348 A1   5/2006 Lee et al.

FOREIGN PATENT DOCUMENTS

| WO | WO 2005/047468 A2 | 5/2005 |
| WO | WO 2006/074222 | * 7/2006 |
| WO | WO 2006/074222 A2 | 7/2006 |
| WO | WO 2007/067151 A1 | 6/2007 |

OTHER PUBLICATIONS

Liu et al. Q-Priming PCR: A quanitative real-time PCR system using a self-quenched BODIPY FL-labeled primer. Analytical Biochemistry 2007;360:154-6; Appendix A, Supplementary Data.*
Gundry et al. Amplicon melting analysis with labeled primers: a closed-tube method for differentiating homozygotes and heterozygotes. Clin Chem 2003;49(3):396-406.*
Behlke et al., "Fluorescence Quenching by Proximal G-Bases," Integrated DNA Technologies, 2005 (3 pages).
Crockett and Wittwer, "Fluorescein-Labeled Oligonucleotides for Real-Time PCR: Using the Inherent Quenching of Deoxyguanosine Nucleotides," *Anal. Biochem.* 290:89-97, 2001.
Kurata et al., "Fluorescent Quenching-Based Quantitative Detection of Specific DNA/RNA Using a BODIPY® FL-Labeled Probe or Primer," *Nucleic Acids Res.* 29:e34 (5 pages), 2001.
Liu and Hong, "Q-Priming PCR: a Quantitative Real-Time PCR System Using a Self-Quenched BODIPY FL-Labeled Primer," *Anal. Biochem.* 360:154-156, 2007.
Misra et al., "Synthesis of Hairpin Probe Using Deoxyguanosine as a Quencher: Fluorescence and Hybridization Studies," *Anal. Biochem.* 364:86-88, 2007.
Nazarenko et al., "Effect of Primary and Secondary Structure of Oligodeoxyribonucleotides on the Fluorescent Properties of Conjugated Dyes," *Nucleic Acids Res.* 30:2089-2195, 2002.
Nobel et al., "The Effect of Overhanging Nucleotides on Fluorescence Properties of Hybridising Oligonucleotides Labelled with Alexa-488 and FAM Fluorophores," *Biophys. Chem.* 113:255-263, 2005.
Tam-Chang et al., "Stem-Loop Probe with Universal Reporter for Sensing Unlabeled Nucleic Acids," *Anal. Biochem.* 366:126-130, 2007.
Whitcombe et al., "Detection of PCR Products Using Self-Probing Amplicons and Fluorescence," *Nature Biotechnol.* 17:804-807, 1999.

* cited by examiner

*Primary Examiner* — Prabha Chunduru
*Assistant Examiner* — Suryaprabha Chunduru
(74) *Attorney, Agent, or Firm* — Klarquist Sparkman, LLP

(57) ABSTRACT

This application provides photoinduced electron transfer (PET) nucleic acid molecules that can be used detect and amplify nucleic acid molecules, such as target nucleic acid molecules. These PET tags can be attached to the 5'-end of a target sequence-specific primer, thereby generating a PET primer. In particular examples, a PET tag includes a 5'-labeled nucleotide that can be quenched by at least two consecutive Gs within the tag sequence, and is unquenched when the PET tag hybridizes with its complementary nucleic acid molecule. Also disclosed are methods of using PET primers in nucleic acid amplification, such as real-time PCR.

9 Claims, 6 Drawing Sheets

PHOTOINDUCED ELECTRON TRANSFER (PET) PRIMER FOR NUCLEIC ACID AMPLIFICATION

CROSS REFERENCE TO RELATED APPLICATION

This is the U.S. National Stage of International Application No. PCT/US2008/084347, filed Nov. 21, 2008, which claims the benefit of the earlier filing date of U.S. Provisional Application No. 60/989,768, filed on Nov. 21, 2007, which is incorporated herein by reference.

FIELD

The present disclosure relates to labeled nucleic acid primers and methods of their use, for example to detect or amplify a target nucleic acid molecule.

BACKGROUND

The real-time polymerase chain reaction (PCR) is currently used as a diagnostic tool in clinical applications, and can be used to obtain quantitative results. The chemistry of real-time PCR is based on monitoring fluorescence at every cycle at a set temperature that facilitates calculating the kinetics of the product formed and performing melting curve analysis to identify formation of the specific product. Fluorescence is usually monitored using an optical device to collect the data at specific excitation and emission wavelengths for the particular fluorophore present in the sample.

One method used to monitor nucleic acid amplification is the addition of intercalating dyes, such as SYBR Green I dye (Ririe et al., *Anal. Biochem.* 245:154-60, 1997) and LCGreen (Wittwer et al., *Clin. Chem.* 49:853-60, 2003) during PCR. During amplification, these dyes are excited with the appropriate wavelength of light, inducing fluorescence when the dye intercalates into a DNA double helix. However, this method does not allow for multiplex reactions.

Specificity can be increased by using a labeled sequence-specific probe. Several of such methods are currently available for performing real-time PCR, such as TaqMan® probes (Lee et al., *Nucleic Acids Res.* 21:3761-6, 1993); molecular beacons (Tyagi and Kramer, *Nat. Biotechnol.* 14:303-8, 1996); self-probing amplicons (scorpions) (Whitcombe et al., *Nat. Biotechnol.* 17:804-7, 1999); Amplisensor (Chen et al., *Appl. Environ. Microbiol.* 64:4210-6, 1998); Amplifluor (Nazarenko et al., *Nucleic Acids Res.* 25:2516-21, 1997 and U.S. Pat. No. 6,117,635); displacement hybridization probes (Li et al., *Nucleic Acids Res.* 30:E5, 2002); DzyNA-PCR (Todd et al., *Clin. Chem.* 46:625-30, 2000); fluorescent restriction enzyme detection (Cairns et al. *Biochem. Biophys. Res. Commun.* 318:684-90, 2004); and adjacent hybridization probes (Wittwer et al., *Biotechniques* 22:130-1, 134-8, 1997).

Some currently available labeled primers can have a secondary structure that is complex and in some instances must be synthesized using specialized procedures. For example, LUX™ primers (Invitrogen Corp.) are fluorescently labeled on the 3'-end and have a stem-loop structure that must be denatured for the primer to work efficiently (especially for reverse transcription). The design of the LUX™ primer is also a time-consuming step, which requires specific software.

Several publications disclose probes that contain only one fluorophore for use in detecting the presence of a particular nucleic acid [for example see U.S. Pat. No. 6,699,661; U.S. Pat. No. 6,495,326; and U.S. Pat. No. 6,492,121 (all to Kurane et al.); U.S. Pat. No. 6,635,427 (Wittwer et al.); Kurata et al. (*Nucl. Acids Res.* 29:E34, 2001); Torimura et al. (*Analyt. Sci.* 17:155-60, 2001); and Crockett et al. (*Analyt. Biochem.* 290:89-97, 2001)]. In these examples, the fluorescent signal is either enhanced or quenched in the presence of the target nucleic acid sequence, depending on the particular design of the probe. In most cases, the labeled primer specifically hybridizes to the target nucleic acid sequence. Similarly, Tam-Chang (*Analyt. Biochem.* 366:126-130, 2007) discloses a multi-probe universal reporter system containing a signal that is enhanced only after sequence-specific hybridization of one of the probes. Guo and Milewicz (*Biotech. Lett.* 25:2079-83, 2003) disclose universal fluorescent tag primers labeled on the 5' end that are not sequence specific. The labeled fluorescent tag universal primer, in combination with two sequence-specific primers, are use to amplify a target nucleic acid sequence.

Yamane (*Nucl. Acids Res.* 30:E97, 2002) discloses a MagniProbe that has an internal fluorophore and an internal intercalator. The fluorescence is quenched by the intercalator in the absence of a target sequence. Upon hybridization with the target sequence, the probe emits fluorescence due to the interference in quenching by intercalation.

Nazarenko et al. (*Nucl. Acids Res.* 30:E37, 2002) disclose a probe with a single fluorophore near the 3' end (but no quencher), and addition of 5-7 base pairs to the 5' end of the sequence-specific probe, wherein the signal from the fluorophore is increased in the presence of the target sequence.

SUMMARY

The present application relates to novel photoinduced electron transfer (PET) nucleic acid molecules (also referred to herein as PET tags). Also provided are methods for using the PET tags, for example in assessing the progress of PCR, such as real time PCR, or for assessing the progress of melting duplex DNA, such as an amplicon. The novel PET tags include a 5'-end-labeled nucleotide, and can further include a target-specific sequence at the 3'-end of the PET tag, thereby generating a labeled sequence-specific primer sequence (also referred to herein as a PET primer). Thus, methods are provided for generating labeled sequence-specific primers, by adding or attaching a primer specific for a target sequence to a labeled PET tag. In the absence of hybridization of the PET tag to is complementary sequence, the detectable signal is altered (such as quenched) by at least two consecutive G nucleotides (or other nucleotides that can permit quenching of the signal from the 5'-end labeled nucleotide, such as isoC and isoG) brought into proximity to the label due to a stem-loop that includes complimentary nucleotide sequences. When the PET tag hybridizes to its complement sequence (e.g., when present in an amplicon), the stem-loop becomes linear, thereby increasing the distance between the label and the at least two consecutive G nucleotides (or isoC or isoG) and alternating the signal from the label (such as increasing the detectable signal).

In particular examples, the disclosed PET nucleic acid molecules include a 5'-end-labeled nucleotide, a stem-loop, and at least two consecutive G nucleotides (or other nucleotides that can permit quenching of the label on the 5'-end nucleotide, such as isoC and isoG), wherein the stem-loop includes complimentary nucleotide sequences in the stem portion, thereby bringing the label on the 5'-end-labeled nucleotide and the at least two consecutive G nucleotides into proximity, thereby changing (such as quenching) a detectable signal from the 5'-end-labeled nucleotide. A target- or sequence-specific primer can be attached to the 3'-end of the PET tag. In some examples, the at least two consecutive G nucleotides adjacent to the stem-loop of the PET tag can be the first two nucleotides at the 5'-end of the target- or sequence-specific primer. In some examples, there are one or more nucleotides (or other spacer) between the sequence-specific primer and the at least two consecutive G nucleotides of the PET tag, such as 1-10 nucleotides. When the PET tag hybridizes with its complementary sequence, the 5'-end-labeled nucleotide is no longer in close proximity to the at least two consecutive G nucleotides, thereby changing the detectable signal from the label (such as increasing the detectable signal).

In particular examples, a PET tag includes the sequence 5'-$X_1X_{2(a)}X_3X_{4(a)}G_x$-3' (SEQ ID NO: 1), wherein $X_1$ is the 5'-end labeled nucleotide, wherein $X_2$ and $X_4$ include complimentary nucleotide sequences of length a, wherein $X_3$ includes the loop of the stem-loop, wherein $G_x$ includes the at least two consecutive G nucleotides. For example, the PET tag can include the sequence 5'-$X_1X_{2(a)}X_3X_{4(a)}G_xX_{5(n)}$-3' (SEQ ID NO: 2), wherein $X_5$ includes "n" number of nucleotides, for example n can be zero or more nucleotides (such as one or more nucleotides, for example 1-5 nucleotides). In some examples, $X_1$ is any nucleotide, but in some examples, $X_1$ is not G. In particular examples, $X_3$ is a trinucleotide sequence, such TAA, ATA, AAT, TTA, TAT, ATT, TTT or AAA. In one example, a PET tag consists of the sequence 5'-$X_1X_{2(a)}X_3X_{4(a)}G_x$-3' (SEQ ID NO: 1) and has a sequence-specific primer (e.g., a primer that specifically hybridizes to a target nucleic acid sequence) attached at its 5'-end to $G_x$. In another example, a PET tag consists of the sequence 5'-$X_1X_{2(a)}X_3X_{4(a)}$-3' (SEQ ID NO: 3) and has sequence-specific primer (e.g., a primer that specifically hybridizes to a target nucleic acid sequence) with at least two consecutive G nucleotides on its 5'-end attached at its 5'-end to $X_{4(a)}$ of the PET tag. Such molecules can be referred to as a labeled sequence-specific primer or a PET primer.

Although particular exemplary PET tags and primers are disclosed herein (for example SEQ ID NOS: 1-3, 10-27, 33 and 35-36), the present application is not limited to these particular sequences.

The signal from the label changes when the PET tag or primer is hybridized to its complementary sequence, for example when it becomes incorporated into an amplicon. The change in the signal can be an increase or a decrease, for example relative to a signal in the absence of the complementary sequence. The resulting change in detectable signal is proportional to the amount of amplicon produced and therefore occurs only when a complimentary stand is synthesized. The signal can be detected by a variety of devices, such as fluorescent microtiter plate readers, spectrofluorometers, fluorescent imaging systems, and real-time PCR instruments.

Any label can be used, such as a fluorophore, for example 6-carboxyfluorescein (6-FAM). In particular examples, a label is one whose signal is significantly decreased in the presence of guanosine, isoG or isoC, such as the ability to quench fluorescence. For example, the nucleotide guanosine can quench a variety of fluorophores, such as 6-FAM. Thus in some examples the label is one that can be quenched by guanosine.

Ideally, a PET tag does not recognize and hybridize to a target nucleic acid sequence in the absence of a sequence-specific primer attached to the 3'-end of the PET tag. For example, if the target nucleic acid sequence is a human p53 sequence, the PET tag does not substantially hybridize to a human p53 sequence. In particular examples, the PET tag alone does not hybridize with a target nucleic acid sequence under moderately stringent or highly stringent hybridization conditions.

The disclosed PET tags can be used to label any sequence-specific primer without significantly affecting the sensitivity of the amplification reaction. Ideally, a sequence-specific primer specifically recognizes a target nucleic acid sequence. For example, if the target sequence is a human p53 sequence, the sequence-specific primer can substantially hybridize to the p53 sequence, but the PET tag does not substantially hybridize to the p53 sequence. In some examples, a sequence-specific primer can hybridize with a target nucleic acid sequence under moderately stringent or highly stringent hybridization conditions.

A PET tag can be attached via its 3'-end (e.g., $G_x$ of SEQ ID NO: 1, $X_{5(n)}$ of SEQ ID NO: 2, or $X4_{(a)}$ of SEQ ID NO: 3) to the 5'-end of a forward primer or a reverse primer specific for the target nucleic acid sequence of interest, thereby generating a labeled forward or labeled reverse primer. The resulting labeled forward or labeled reverse primer can be used to amplify the appropriate target nucleic acid, for example using real-time PCR, resulting in the formation of amplicon products. The method can further include quantifying an amount of target nucleic acid sequence present in a sample.

Also provided by the present disclosure are kits that include one or more PET nucleic acid molecules of the present disclosure. The kits can further include a ligase to permit joining of the 3'-end of a PET tag to the 5'-end of a target sequence-specific forward or reverse primer. In some examples, the kit includes one or more sequence-specific forward or reverse primers, such as primers that recognize and can be used to amplify a target sequence of interest. In a specific example, the sequence-specific forward or reverse primer hybridizes specifically to a pathogen's nucleic acid sequence, such as a viral, bacterial, parasitic, or fungal nucleic acid sequence. In another specific example, the sequence-specific forward or reverse primer hybridizes specifically to a human nucleic acid sequence, such as a sequence associated with a disease (such as cancer or a hereditary disorder).

Arrays, such as a DNA microarray, that include one or more of the disclosed PET nucleic acid molecules are encompassed by this disclosure. Such arrays can be used to determine whether a desired target sequence is present, such as in a sample. The disclosed PET primers can be hybridized to a target nucleic acid sequence attached to the array (for example resulting in fluorescence). In other examples, one or more of the disclosed PET tags or primers are attached to the array.

The disclosed PET tags, for example when attached to a sequence that can hybridize to a target sequence (and thereby producing a PET primer), provide an approach to detect, and in some examples further quantify, a target nucleic acid. Use of the PET primers is shown herein to provide a highly sensitive detection method, which permits detection of small quantities of target nucleic acid molecule, such as DNA. For example, the present disclosure provides methods of detecting a target nucleic acid molecule. The method can include incubating a sample containing nucleic acids (such as DNA or RNA) with a PET tag which is linked to a forward or a reverse target sequence specific primer, and with the corresponding forward or reverse target sequence specific primer not containing the PET tag. The sample and labeled forward primer and reverse primer not containing the PET tag, or forward primer not containing the PET tag and labeled reverse primers are incubated under conditions sufficient to permit amplification of the target nucleic acid. A change in signal from the label on the resulting PET primer is monitored, wherein a change in signal (such as an increase or decrease in signal), indicates the presence of the target nucleic acid sequence. In particular examples, both the forward and reverse target sequence specific primers contain a PET tag.

In some examples, the change in signal is monitored during the amplification reaction, for example in real time as the amplicons are formed. In other or additional examples, the change in signal is monitored after the amplification, for example by exposing the resulting amplicons to increased temperature to generate a melting curve. Melting curve analysis can be used to confirm the presence of a target nucleic acid, and can also be used to distinguish polymorphisms in amplicons.

Those skilled in the art will appreciate that the disclosed isolated nucleic acid molecules and methods can be used to amplify two or more different target nucleic acid molecules (such as at least 2, at least 3, at least 4, or even at least 5 different nucleic acid sequences) in the same amplification reaction. In particular examples, two or more different PET primers, each containing a different fluorophore, are used. In other examples, the same PET tag and label are attached to at least two different sequence-specific primers, wherein the resulting amplicons are differentiated, for example by using melting curve analysis. In yet other examples, combinations of the same PET tag sequence and label or different PET tag sequences and labels are used.

The foregoing and other objects and features of the disclosure will become more apparent from the following detailed description, which proceeds with reference to the accompanying figures.

SEQUENCE LISTING

Figure 1A:
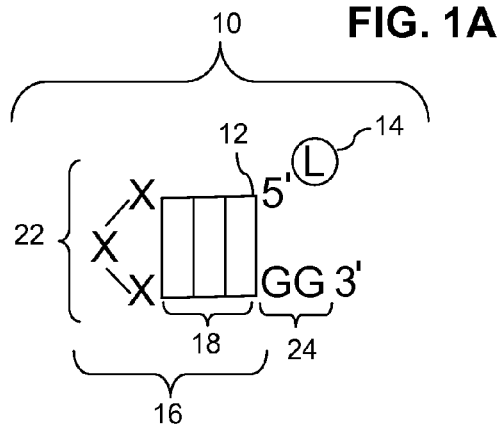
FIGS. 1A and B are schematic drawings showing exemplary PET tags 10 in the non-hybridized configuration.

The nucleotide sequences of the nucleic acids described herein are shown using standard letter abbreviations for nucleotide bases. Only one strand of each nucleic acid sequence is shown, but the complementary strand is understood as included by any reference to the displayed strand.

SEQ ID NO: 1 is the nucleic acid sequence for exemplary PET tag 5'-$X_1X_{2(a)}X_3X_{4(a)}G_x$-3';

SEQ ID NO: 2 is the nucleic acid sequence for exemplary PET tag 5'-$X_1X_{2(a)}X_3X_{4(a)}G_xX_{5(n)}$-3'.

SEQ ID NO: 3 is the nucleic acid sequence for exemplary PET tag 5'-$X_1X_{2(a)}X_3X_{4(a)}$-3'.

SEQ ID NO: 4 is the nucleic acid sequence for exemplary PET tag 5'-TAMRA-AGGCGCATAGCGCCTGG-3'.

SEQ ID NO: 5 is the nucleic acid sequence for the C. parvum 18S ss rRNA sequence-specific reverse primer CryJVR 5'-ATTCCCCGTTACCCGTCA-3'.

SEQ ID NO: 6 is the nucleic acid sequence for the C. parvum 18S ss rRNA sequence-specific forward primer CryJVF 5'-GGTGACTCATAATAACTTTACGGAT-3'.

SEQ ID NOS: 7 and 8 are a forward and a reverse primer for TaqMan™ amplification of the C. parvum 18S ss rRNA gene, respectively.

SEQ ID NO: 9 is a TaqMan™ probe for detection of the amplified C. parvum 18S ss rRNA gene.

SEQ ID NOS: 10-27 are exemplary PET tags attached to a sequence-specific primer for C. parvum 18S ss rRNA (ACTCATAATAACTTTACGGAT; nucleotides 20-40 of SEQ ID NO: 10). One skilled in the art will appreciate the PET tag portion of SEQ ID NOS: 10-27 can be attached to other sequence-specific primers.

SEQ ID NOS: 28 and 29 are exemplary PET tag sequences.

SEQ ID NOS: 30-32 are PET primers that include a PET tag with zero, one or two 3'-end G nucleotides, respectively, attached to a sequence-specific primer for C. parvum 18S ss rRNA (ATGACGGGTAACGGGGAAT; SEQ ID NO: 7). One skilled in the art will appreciate that the PET tag portion can be attached to other sequence-specific primers.

SEQ ID NO: 33 is a reverse sequence-specific primer that can be used in combination with SEQ ID NOS: 30-32 to amplify C. parvum 18S ss rRNA.

SEQ ID NOS: 34-35 are PET forward and reverse primers, respectively, that include a sequence-specific primer for C. parvum 18S ss rRNA. One skilled in the art will appreciate the PET tag portion can be attached to other sequence-specific primers.

SEQ ID NO: 36 is a Quas670 probe specific for C. parvum 18S ss rRNA.

SEQ ID NOS: 37-38 are PET forward and reverse primers, respectively, that include a sequence-specific primer for C. parvum 18S ss rRNA. One skilled in the art will appreciate the PET tag portion can be attached to other sequence-specific primers.

DETAILED DESCRIPTION OF SEVERAL EMBODIMENTS

Abbreviations and Terms

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a nucleic acid molecule" includes single or plural nucleic acid molecules and is considered equivalent to the phrase "comprising at least one nucleic acid molecule." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

CT: crossing or cycle threshold)
PCR: polymerase chain reaction
PET: photoinduced electron transfer 3'-end: The end of a nucleic acid molecule that does not have a nucleotide bound to it 3' of the terminal residue. In some examples, a PET tag includes two or more G nucleotides at its 3'-end. In some example, a PET tag is covalently linked or otherwise attached at its 3'-end to the 5'-end of a sequence-specific primer directed to a target nucleic acid.

5'-end: The end of a nucleic acid sequence where the 5'-position of the terminal residue is not bound by a nucleotide.

5'-end labeled nucleotide: The terminal residue at the 5'-end of a nucleic acid molecule possessing a label (such as a label that is covalently attached) capable of emitting a detectable signal. The label can be incorporated by enzymatic modification of the terminal nucleotide after isolation of the nucleic acid molecule. In particular examples, the label can be a constituent moiety of a modified nucleotide substrate used in the synthesis of the nucleic acid molecule. In such examples, the label can be incorporated into the nucleotide at any position (such as the α, β, or γ phosphate or the sugar) so long as it does not significantly interfere with polynucleotide synthesis.

Amplifying a nucleic acid molecule: To increase the number of copies of a nucleic acid molecule. The resulting amplification products are called "amplicons." In a particular example, a target nucleic acid molecule is amplified using the polymerase chain reaction (PCR) whereby a forward primer and a reverse primer are incubated with a target nucleic acid sequence under repeated cycles of DNA denaturation, annealing and primer extension. During primer extension, the primers are utilized by a DNA polymerase in the synthesis of a DNA strand complementary to the target nucleic acid. Thus, each resulting DNA amplicon contains either a newly-extended forward primer or reverse primer. A primer extension cycle is completed when the sample incubation conditions are changed to denature the newly synthesized dsDNA.

Complementary: Complementary binding occurs when a nucleotide forms a hydrogen bond to another nucleotide. In one example, the complementary nucleotides are present on a single nucleic acid molecule; for example causing this nucleic acid molecule to form a secondary structure such as a hairpin loop. In other examples, the complementary nucleotides are present on two different nucleic acid molecules, such as single-stranded DNA molecules, for example thereby forming a duplex (e.g., double-stranded DNA). Normally, the base adenine (A) is complementary to thymidine (T) and uracil (U), while cytosine (C) is complementary to guanine (G). For example, the sequence 5'-ATCG-3' of one portion of a nucleic acid molecule can bond to 3'-TAGC-5' of another portion of the same nucleic acid molecule, for example to form a section of dsDNA. In this example, the sequence 5'-ATCG-3' is the reverse complement of 3'-TAGC-5'.

Nucleic acid molecules can be complementary to each other even without complete hydrogen-bonding of all bases of each molecule. For example, hybridization with a complementary nucleic acid sequence can occur under conditions of differing stringency in which a complement will bind at some but not all nucleotide positions. In particular examples disclosed herein, the complementary sequences comprising a stem-loop structure are sufficiently complementary to maintain the stem structure even though one or more base pairs within the stem are non-complementary.

Denaturation: The conversion of one or more molecules from a folded to a linear physical conformation. Denaturation also refers to the separation of a partially or completely double-stranded nucleic acid molecule into its single-stranded constituents. Molecular denaturation can occur upon changes in temperature, salt concentration, or pH as described in Sambrook et al. (Molecular Cloning: A Laboratory Manual, Cold Spring Harbor, N.Y., 2001) and Ausubel et al. (In Current Protocols in Molecular Biology, John Wiley & Sons, New York, 1998).

In particular examples, dsDNA is denatured into ssDNA during PCR by elevating the incubation temperature to 94° C. or greater for at least one minute.

Detectable Signal: An indicator, such as a detectable physical quantity from which information can be obtained. In one example, a label emits a signal capable of detection, such as a fluorescent signal. When a label is incorporated uniformly into a group of molecules, the presence of its detectable signal can be directly correlated with the number of molecules in a given sample. In some examples the detection of the signal is dependant on the molecular context within which the signal is found, such as its proximity to a molecular quencher. In other examples, such as particular fluorescent signals, the detection of the signal requires external stimulus (for example, a particular wavelength of light) for generation of the signal.

Fluorophore: A chemical compound, which when excited by exposure to a particular wavelength of light, emits light (fluoresces), for example at a different wavelength of light. Exemplary fluorophores include, but are not limited to: 6-carboxyfluorescein (6-FAM™ dye); 5-carboxyfluorescein (5-FAM™ dye); boron dipyrromethene difluoride (BODIPY® dye); N,N,N',N'-tetramethyl-6-carboxyrhodamine (TAMRA™ dye); acridine, stilbene, 6-carboxy-fluorescein hexachloride (HEX™ dye), TET™ dye (Tetramethyl fluorescein), 6-carboxy-X-rhodamine (ROX™ dye), ALEXA FLUOR® 488, Texas Red® dye, 2',7'-dimethoxy-4',5'-dichloro-6-carboxyfluorescein (JOE™ dye), Cy3® dye, Cy5® dye, VIC® dye (Applied Biosystems), LC Red 640, LC Red 705, Yakima yellow, as well as derivatives thereof. Any fluorophore can be used with the PET tags disclosed herein.

Also encompassed by the term "fluorophore" are luminescent molecules, which are chemical compounds which do not require exposure to a particular wavelength of light to fluoresce; luminescent compounds naturally fluoresce. Therefore, the use of luminescent signals can eliminate the need for an external source of electromagnetic radiation, such as a laser.

A particular type of fluorophore is one whose fluorescence is quenched in the presence of guanine (G), such as 6-FAM™ dye; 5-FAM™ dye; HEX™ dye; ALEXA FLUOR® 488; boron dipyrromethene difluoride (BODIPY® dye); or N,N, N',N'-tetramethyl-6-carboxyrhodamine (TAMRA™ dye). In one example, fluorescence is quenched in the presence of guanine by at least 25%, such as at least 50%, at least 75%, at least 80%, or at least 90%, as compared to an amount of fluorescence in the absence of guanine (wherein both are in the presence of the appropriate excitation wavelength of light).

Hybridization: Hybridization of a nucleic acid occurs when two complementary nucleic acid molecules undergo an amount of hydrogen bonding to each other, or two different regions of a single nucleic acid molecule undergo an amount of hydrogen bonding to one another. The stringency of hybridization can vary according to the environmental conditions surrounding the nucleic acids, the nature of the hybridization method, and the composition and length of the nucleic acids used. Calculations regarding hybridization conditions required for attaining particular degrees of stringency are discussed in Sambrook et al., *Molecular Cloning: A Laboratory Manual* (Cold Spring Harbor Laboratory Press, Cold Spring Harbor, N.Y., 2001); and Tijssen, *Laboratory Techniques in Biochemistry and Molecular Biology—Hybridization with Nucleic Acid Probes* Part I, Chapter 2 (Elsevier, N.Y., 1993). The $T_m$ is the temperature at which 50% of a given strand of nucleic acid is hybridized to its complementary strand.

Increase in signal: To become greater in some way. A detectable increase is one that can be detected, such as an increase in the intensity, frequency, or presence of an electromagnetic signal, such as fluorescence. In particular examples, the detectable increase can be directly correlated to the presence of a target nucleic acid molecule and additionally to the quantity of a target nucleic acid molecule. In other particular examples, differences in the increase of signal within a population of molecules are indicative of polymorphisms within that population.

Isolated: An "isolated" biological component (such as a nucleic acid molecule) has been substantially separated, produced apart from, or purified away from other biological components such as cells. Nucleic acid molecules which have been "isolated" include nucleic acids molecules purified by standard purification methods, as well as those chemically synthesized. Isolated does not require absolute purity, and can include nucleic acid molecules that are at least 50% isolated, such as at least 75%, at least 80%, at least 90%, at least 95%, at least 98%, at least 99% or even 100% isolated.

Label: An agent capable of detection, for example by spectrophotometry, flow cytometry, or microscopy. For example, a label can be attached to a nucleotide, thereby permitting detection of the nucleotide, such as detection of the nucleic acid molecule of which the nucleotide is a part of (e.g., a PET tag or PET primer). Examples of labels include, but are not limited to, radioactive isotopes, enzyme substrates, co-factors, ligands, chemiluminescent agents, fluorophores, haptens, enzymes, and combinations thereof. In some examples the label is one whose signal can be quenched by two or more G nucleotides. Methods for labeling and guidance in the choice of labels appropriate for various purposes are discussed for example in Sambrook et al. (Molecular Cloning: A Laboratory Manual, Cold Spring Harbor, New York, 2001) and Ausubel et al. (In Current Protocols in Molecular Biology, John Wiley & Sons, New York, 1998).

Ligase: An enzyme that can catalyze the joining of two molecules ("ligation") by forming a new chemical bond. An exemplary ligase is DNA ligase, which can link two nucleic acid molecules (e.g., a PET tag and a sequence-specific primer) by forming a phosphodiester bond between the two molecules.

Nucleic acid molecule: A deoxyribonucleotide or ribonucleotide polymer, which can include analogues of natural nucleotides that hybridize to nucleic acid molecules in a manner similar to naturally occurring nucleotides. In a particular example, a nucleic acid molecule is a single-stranded (ss) DNA or RNA molecule, such as a primer, cDNA, amplicon, or transcription product. In another particular example, a nucleic acid molecule is a double-stranded (ds) molecule, such as cellular genomic DNA or viral genomic RNA.

Nucleotide: The fundamental unit of nucleic acid molecules. A nucleotide includes a nitrogen-containing base attached to a pentose monosaccharide with one, two, or three phosphate groups attached by ester linkages to the saccharide moiety.

The major nucleotides of DNA are deoxyadenosine 5'-triphosphate (dATP or A), deoxyguanosine 5'-triphosphate (dGTP or G), deoxycytidine 5'-triphosphate (dCTP or C) and deoxythymidine 5'-triphosphate (dTTP or T). The major nucleotides of RNA are adenosine 5'-triphosphate (ATP or A), guanosine 5'-triphosphate (GTP or G), cytidine 5'-triphosphate (CTP or C) and uridine 5'-triphosphate (UTP or U).

Nucleotides include those nucleotides containing modified bases, modified sugar moieties and modified phosphate backbones, for example as described in U.S. Pat. No. 5,866,336 to Nazarenko et al. PET tags and sequence-specific primers can include one or more modified bases, modified sugar moieties or modified phosphate backbones.

Examples of modified base moieties which can be used to modify nucleotides at any position on its structure include, but are not limited to: 5-fluorouracil, 5-bromouracil, 5-chlorouracil, 5-iodouracil, hypoxanthine, xanthine, acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N~6-sopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl)uracil, and 2,6-diaminopurine.

Examples of modified sugar moieties which can be used to modify nucleotides at any position on its structure include, but are not limited to: arabinose, 2-fluoroarabinose, xylose, and hexose, or a modified component of the phosphate backbone, such as phosphorothioate, a phosphorodithioate, a phosphoramidothioate, a phosphoramidate, a phosphordiamidate, a methylphosphonate, an alkyl phosphotriester, or a formacetal or analog thereof.

In particular examples, a nucleotide can be modified prior to incorporation into a growing nucleic acid chain so as to possess a label capable of emitting a detectable signal. Ideally, such modifications allow for incorporation of the nucleotide into a growing nucleic acid chain. That is, they do not terminate nucleic acid synthesis. In other particular examples, a nucleotide is modified after synthesis of the nucleic acid molecule. An exemplary nucleotide modification is the covalent attachment of a fluorophore.

Polymorphism: A variation in the nucleic acid sequence within a population of molecules. Polymorphisms may be differences in consecutive or non-consecutive nucleotides within a particular sequence. In particular examples, a polymorphism is a difference in a single base pair. In other examples a polymorphism is 5, 10, 20, or greater differences in nucleotide identity. In other examples a polymorphism may be a deletion of sequence, an insertion of sequence, or an inversion of sequence. Sequence differences in polymorphic nucleic acids will result in differences in the rate and temperature at which the polymorphic molecules will denature from dsDNA to ssDNA and anneal into dsDNA from ssDNA. In one example, a target sequence can contain one or more polymorphisms, such as a polymorphism associated with disease.

Primer: A short nucleic acid molecule, such as an 8-nucleotide long DNA or RNA oligonucleotide. Longer primers can be about 10, 12, 15, 20, 25, 30 or 50 nucleotides or more in length, such as 10-75, 10-50, 10-25, 10-20, 10-15, 12-50 or 12-20 nucleotides. Primer extension occurs when a primer is used to initiate the synthesis of a longer nucleic acid sequence. Primers can be annealed to a complementary target DNA strand by nucleic acid hybridization to form a hybrid between the primer and the target DNA strand. The primer is then extended along the template target DNA strand by a DNA polymerase enzyme. Forward and reverse primers can be used for amplification of a nucleic acid sequence, for example by PCR or other nucleic acid amplification methods.

Specificity of a primer for a target nucleic acid increases with the length of complementary sequence possessed by the primer. Thus, for example, a primer that includes 30 consecutive complementary nucleotides will anneal to a target sequence with greater specificity than a corresponding primer of only 15 complementary nucleotides. Thus, to obtain greater specificity, probes and primers can be selected that include at least 20, 25, 30, 35, 40, 45, 50 or more consecutive complementary nucleotides. Conversely, a PET tag described herein is a primer that possesses little or no complementary sequence to a target nucleic acid molecule, such that it is unable to hybridize to the target molecule under conditions of moderate or high stringency.

In particular examples, a 5'-end labeled PET tag can be covalently attached at its 3'-end to the 5'-end of a sequence-specific primer.

Photoinduced Electron Transfer (PET) primer: A PET tag covalently attached at its 3'-end to a sequence-specific primer, such that under conditions suitable for nucleic acid amplification, the hairpin is denatured, moving the 5'-end label out of proximity from the at least two adjacent G residues, allowing the 5'-end label to emit a detectable signal.

Photoinduced Electron Transfer (PET) tag: A short nucleic acid molecule containing a stem-loop structure, wherein the stem-loop structure positions a 5'-end label into proximity with at least two adjacent G residues (e.g., at the 3'-end of the PET tag) such that the G residues quench a detectable signal from the 5'-end label. In particular examples a PET tag is at least 10 nucleotides, at least 12 nucleotides, such as 10-20 nucleotides, for example 12, 13, 14 or 15 nucleotides.

Proximity: A measure of nearness, for example when a detectable signal from a label is quenched if the label is in sufficient proximity to the quencher of that label. In particular examples, the detectable signal from the 5'-end label of a PET tag is significantly quenched when placed into proximity with at least two adjacent G residues.

Quantifying a nucleic acid molecule: Determining or measuring a quantity (such as a relative quantity) of a nucleic acid molecule present, such as the number of amplicons or the number of nucleic acid molecules present in a sample. In particular examples, it is determining the relative amount or actual number of nucleic acid molecules present in a sample.

Quencher: A molecular species that can reduce a detectable signal from a label. In particular examples, a quencher can be at least two consecutive G residues that quench the signal from a label at the 5'-end of a PET primer or PET tag.

Quenching a signal: A reduction of detectable signal from a label, such as a reduction in fluorescence emission. For example, quenching of a detectable fluorescent signal emitted from a label at the 5'-end-labeled nucleotide on a PET tag occurs when the label, through sequence-directed secondary structure, is placed in sufficient proximity to a quencher (such as at least two consecutive G residues) that the quencher reduces the detectable signal from the label on the 5'-end labeled nucleotide.

Real-time quantitative PCR: A method for detecting and measuring products generated during each cycle of a PCR, which are proportionate to the amount of template nucleic acid prior to the start of PCR. The information obtained, such as an amplification curve, can be used to quantitate the initial amounts of template nucleic acid sequence.

Sample: Biological specimens such as samples containing biomolecules, for example nucleic acid molecules (e.g., genomic DNA, cDNA, RNA, or mRNA). Exemplary samples are those containing cells or cell lysates from a subject, such as those present in peripheral blood (or a fraction thereof such as serum), urine, saliva, tissue biopsy, cheek swabs, surgical specimen, fine needle aspirates, amniocentesis samples and autopsy material.

Sequence-specific primer: A short nucleic acid molecule possessing sequence that can substantially hybridize with a target nucleic acid molecule under moderately stringent or highly stringent conditions. In particular examples, a sequence-specific primer is covalently attached at its 5'-end to the 3'-end of a PET tag can be used to detect the presence of a target nucleic acid molecule. In other examples, a sequence-specific primer is used for location-specific amplification of a target nucleic acid molecule using PCR. In some examples, a sequence-specific primer is at least 8 nucleotides, such as at least 10, at least 15, at least 20 nucleotides, for example 8-50, 8-25, 8-20, 8-15, 10-20, or 12-20 nucleotides.

Signal: An indicator, such as a detectable physical quantity from which information can be obtained. In one example, a label emits a signal capable of detection, such as a fluorescent signal.

Stem-loop: As shown in FIGS. 1A and 2, a molecular secondary structure wherein two portions of a linear molecule (e.g., 20 of FIG. 2) possess sufficient affinity (e.g., complementarity) to fold into a double-stranded stem (e.g., 18 of FIGS. 1A and 1B) that is connected by a single-stranded loop (e.g., 22 of FIGS. 1A and 1B). A nucleic acid stem-loop is the result of two inverted repeat sequences connected by three or more nucleotides. In particular examples, the inverted repeats are less than 100% complementary, but the overall sequence is sufficiently complementary to maintain the stem structure.

Target nucleic acid sequence or molecule: A pre-selected nucleic acid molecule, for example whose detection or sequence is desired. The target nucleic acid molecule need not be in a purified form. Various other biomolecules can also be present with the target nucleic acid molecule. For example, the target nucleic acid molecule can be present in a cell or a biological sample (which can include other nucleic acid molecules and proteins).

Under conditions sufficient for: A phrase that is used to describe any environment that permits the desired activity. An example includes incubating forward and reverse primers with a sample under conditions sufficient to allow amplification of a target nucleic acid molecule in the sample. Another particular example includes conditions sufficient for determining whether the target nucleic acid molecule is present in a sample, such as a target nucleic acid molecule containing one or more polymorphisms.

Photoinduced Electron Transfer (PET) Tags and Primers and Methods of Making

Disclosed herein are photoinduced electron transfer (PET) nucleic acid molecules (referred to herein as PET tags and PET primers) that can be used in nucleic acid amplification to detect the presence of a target nucleic acid molecule. The PET tag sequence is generic and without significant specificity for any particular nucleic acid sequence. For example, rather than hybridize specifically to a target nucleic acid, PET tags can be ligated or synthesized at their 3'-end to a forward and/or reverse amplification primer that contains significant sequence specificity for the target nucleic acid molecule. The resulting nucleic acid (referred to here as a PET primer) can be used to detect a target nucleic acid molecule.

Upon incorporation of a PET primer (e.g., one that is covalently attached to a target-specific sequence) into a newly-synthesized amplicon, a quenched detectable signal from a label at the PET primer 5'-end is moved away from quenching nucleotides contained therein. The signal is thus de-quenched and detectable, and indicates the presence of the target nucleic acid. In some examples, the signal can be detected after each amplification cycle to quantitate the amount of amplified target nucleic acid in real time, as in real-time PCR or real time RT-PCR. In other examples, the signal can be detected after amplification is completed. In other particular examples the signal from the incorporated PET primer can be used to detect the presence of nucleotide polymorphisms, for example by monitoring the signal during amplicon denaturation by methods well known to the art. Although particular PET tag sequences are provided herein (e.g., see Table 2), the disclosure is not limited to these specific examples.

Figure 1B:
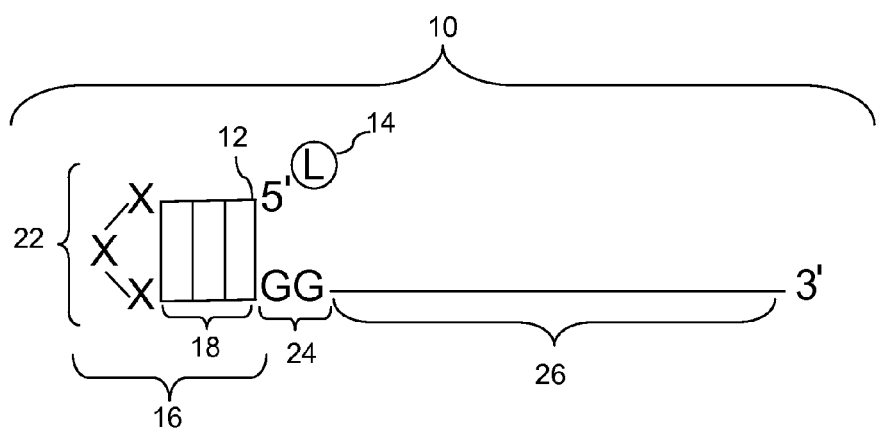
Figure 2:
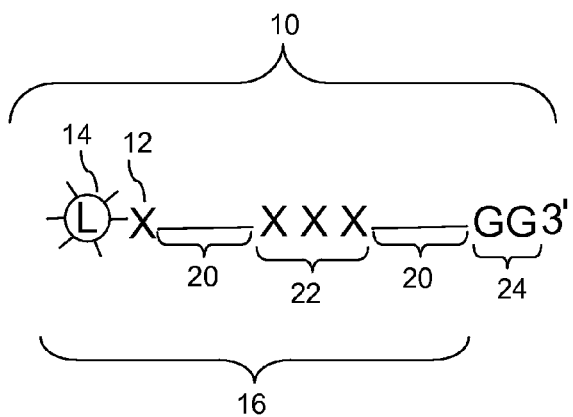
FIG. 2 is a schematic drawing showing an exemplary PET tag 10 in the hybridized configuration during or after nucleic acid amplification (e.g., when part of an amplicon).

FIGS. 1A-B and 2 show an exemplary PET nucleic acid molecule tag when not hybridized to its complementary sequence (e.g., stem-loop structure present), and when hybridized to its complementary sequence (e.g., stem-loop structure absent) as part of an amplicon, respectively. The PET tag 10 includes a 5'-end nucleotide 12 with a label 14 capable of emitting a detectable signal. The 5'-end label 14 is located at the base of a stem-loop structure 16, the stem 18 of which is formed by two inverted repeats (20, FIG. 2) of sufficient length and complementary nucleotide sequence to anneal one to another. Each inverted repeat 20 is separated by three or more non-complementary nucleotides to form the loop 22 of the stem-loop. The structure of the stem-loop is such that the 5'-end label 14 is positioned into proximity with at least two consecutive G nucleotides (or isoC or isoG) 24 located at the 3'-end of the stem-loop structure. The proximity of the G nucleotides 24 to the 5'-end label 14 quenches the detectable signal from the label 14. The 3'-end portion of the PET tag 10 follows the at least two consecutive G nucleotides 24. In some examples, the PET tag includes one or more nucleotides 26 after the at least two consecutive G nucleotides 24, such as 1-50 nucleotides, such as 1, 2, 3, 4, 5, or nucleotides.

The 5'-end nucleotide 12 can be any nucleotide that can be covalently modified to contain a label with a detectable signal. In particular examples, the 5'-end nucleotide 12 is a T, A, G, or C nucleotide. In other particular examples, the 5'-end nucleotide 12 is a T, A, or C nucleotide. In other particular examples, the 5'-end nucleotide 12 is any nucleotide except G. In particular examples, the 5'-end nucleotide 12 is any nucleotide analog that contains a label 14 that emits a detectable signal.

The 5'-end label 14 can be any label that is capable of emitting a detectable signal. In particular examples, the 5'-end label 14 is a fluorophore. In one example, the fluorophore emits a fluorescent signal that is quenched when the label is brought into proximity of the at least two consecutive G nucleotides 24. The signal can be decreased by any detectable amount, such as at least 10%, at least 30%, at least 50%, at least 70%, at least 90%, or even 100%. Particular examples of fluorophores that can be used include, but are not limited to, 6-carboxyfluorescein (6-FAM™ dye); 5-carboxyfluorescein (5-FAM™ dye); boron dipyrromethene difluoride (BODIPY® dye); N,N,N',N'-tetramethyl-6-carboxyrhodamine (TAMRA™ dye); ALEXA FLUOR® 488; acridine; stilbene; 6-carboxyfluorescein hexachloride (HEX™ dye); TET™ dye; ROX™ dye; Texas Red® dye; JOE™ dye; Cy3® dye; Cy5® dye; VIC® dye; LC Red 640; LC Red 705; Yakima yellow; as well as derivatives thereof. In another example, the label is not a quencher.

The 5'-end label 14 can be covalently attached to the PET tag 10 at any available moiety of the 5'-end nucleotide 12. In particular examples, the 5'-end label 14 is covalently attached at the triphosphate of the 5'-end nucleotide 12. In other particular examples, the 5'-end label 14 is covalently attached at any available moiety of the nitrogenous base of the 5'-end nucleotide 12. In other particular examples, the 5'-end label 14 is covalently attached to any available moiety of the sugar component of the 5'-end nucleotide 12. Covalent attachment of the 5'-end label 14 to the triphosphate, nitrogenous base, or sugar of the 5'-end nucleotide 12 can be accomplished according to standard methodology well known in the art as discussed, for example in Sambrook et al. (Molecular Cloning: A Laboratory Manual, Cold Spring Harbor, N.Y., 2001) and Ausubel et al. (In Current Protocols in Molecular Biology, John Wiley & Sons, New York, 1998).

The 5'-end nucleotide 12 is located at the base of a stem-loop structure 16. The stem-loop 16 (linear in FIG. 2) functions to bring the 5'-end label 14 within proximity of the at least two consecutive G nucleotides 24, which quench the signal from the label 14. The stem 18 of the stem loop structure 16 is composed of two lengths of nucleotide sequence 20 (FIG. 2) that are of sufficient complementarity one to another to stably base pair. In particular examples, the stem 18 can be composed of two inverted repeats 20 of 100% complementarity to each other. In other particular examples, the stem 18 is composed of sequences 20 that are at least 50%, at least 60%, at least 70%, at least 80%, at least 90%, or at least 95% complementary to each other. The length of the stem 18 can be any number of nucleotides, so long as the stem can be stably maintained under non-denaturing conditions. In particular examples each of the component sequences portions 20 of the stem 18 is at least 3, at least 4 at least 5, at least 6, at least 7, at least 8, or at least 9 nucleotides, such as 3, 4, 5, 6, 7, 8, 9, or 10 nucleotides. In other particular examples each of the two component sequences 20 of the stem 18 is 10 or more nucleotides. In some examples, each of the two component sequences 20 of the stem 18 is 3-5 or 3-10 nucleotides.

The loop 22 of the stem-loop structure 16 connects the two component sequences 20 of the stem. The loop 22 can be composed of any number of nucleotides and any sequence such that the stem-loop structure 16 is maintained in order to quench the detectable signal from the 5'-end label 14 as described herein. In particular examples, the loop 22 is 3, 4, 5, or 6 nucleotides. In other particular examples, the loop 22 is at least 7 nucleotides, such as 7-12 nucleotides. In other particular examples, the loop 22 is at least 10 nucleotides. In particular examples, the loop 22 can be any trinucleotide sequence. In other particular examples, the loop 22 does not contain C or G nucleotides. In other particular examples, the loop 22 can be any trinucleotide sequence that does not contain C or G nucleotides. In other particular examples, the loop 22 is TAA, ATA, AAT, TTA, TAT, ATT, TTT, or AAA.

In particular examples, the PET tag 10 includes at least two consecutive G nucleotides 24 at the 3'-end of the stem-loop structure 16. However, in some examples the at least two consecutive G nucleotides are instead present at the 5'-end of a sequence-specific primer attached to the 3'-end of the PET tag. One skilled in the art will appreciate that isoC or isoG can be used alternatively or in addition to G. The G nucleotides 24 quench the detectable signal from the 5'-end label 14 when the 5'-end label 14 is brought into proximity with the consecutive G nucleotides 24 by the stem-loop structure 20 (see FIGS. 1A and B). However, when the PET tag is hybridized to its complementary sequence (for example when incorporated into an amplicon), the stem-loop structure 16 linearizes moving the G nucleotides 24 away from proximity to label 14, and thus the G nucleotides 24 cannot significantly quench the detectable signal from the 5'-end label 14 and the detectable signal from the label 14 is emitted and can be detected (see FIG. 2). In particular examples, the consecutive G nucleotides 24 can include 2, 3, 4, 5, or 6 consecutive G nucleotides. In other particular examples the consecutive G nucleotides 24 include at least 7 consecutive G nucleotides. As shown in FIG. 2, in a particular example, the PET tag stem-loop structure 16 is linearized as a result of its incorporation into a nucleic acid amplicon.

As shown in FIG. 1B, the PET tag in some examples includes additional nucleotides 26 at the 3'-end of the PET tag following the at least two consecutive G nucleotides 24. For example, the additional nucleotides 26 can be composed of 0, 1, 2, 3, 4, 5, 8, 10, 15, 20 or more nucleotides, such as at least 8 nucleotides.

In specific embodiments, the PET tags 10 disclosed herein can be at least 12 nucleotides in length, such as 12 to 20 nucleotides, for example 12, 13, 14, 15, 16, 17, 18, 19, or 20 nucleotides in length. In other specific examples, the PET tags can be between 22 and 30 nucleotides long, such as 22, 23, 24, 25, 26, 27, 28, 29, or 30 nucleotides. In other specific examples the PET tags 10 can be 35, 40, 45, or 50 nucleotides long.

Figure 3A:
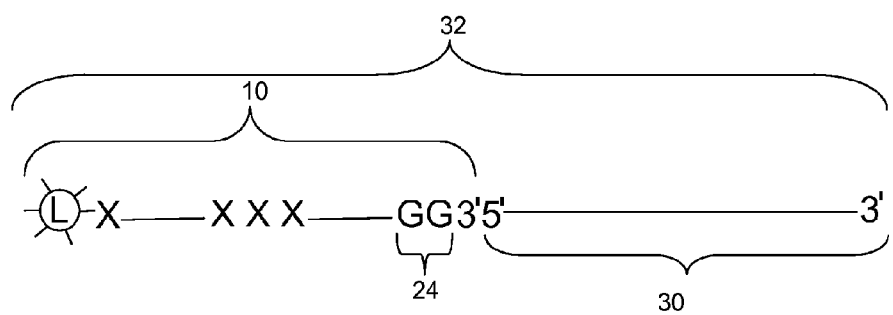
FIGS. 3A and B are schematic drawings showing exemplary PET tags 10 ligated or synthesized at the 3'-end to the 5'-end of a sequence-specific primer 30 to generate a labeled sequence-specific primer (or PET primer) 32 which can be used in the methods disclosed herein. These drawings generally show the PET primer as it would look as part of an amplicon.
Figure 3B:
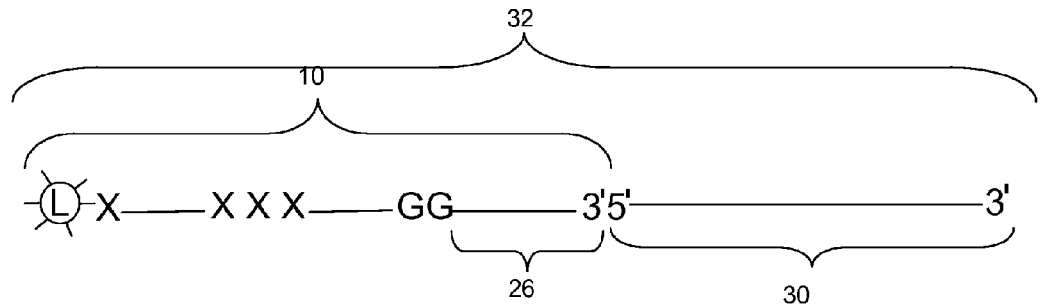

As shown in FIGS. 3A and 3B, a PET tag 10 can be linked (e.g., ligated, synthesized, or attached) at its 3'-end to the 5'-end of a sequence-specific primer sequence 30, thereby generating a labeled sequence-specific primer sequence 32 (also referred to herein as a PET primer). Such PET primers can be generated using routine methods, such as by synthesizing a nucleic acid molecule that includes a PET tag and a sequence-specific primer, or by ligating a PET tag to a sequence-specific primer. In some examples, the target-specific primer 30 is added to the PET tag 10 via the at least two consecutive G nucleotides 24 (FIG. 3A). In other examples, the target-specific primer 30 is added to the PET tag 10 via additional nucleotides 26 (FIG. 3B). The labeled sequence-specific primer 32 (which in some examples is isolated) can then be used in an amplification reaction, such as a PCR or an RT-PCR reaction. The sequence-specific primer 30 can recognize a target nucleic acid of interest, such as a pathogen nucleic acid sequence, for example a viral, fungal, bacterial, or parasitic DNA or RNA sequence. In another example, a target nucleic acid sequence, such as a DNA or RNA sequence, is a nucleic acid sequence whose expression is altered in response to a disease, such as cancer. In some examples, the target nucleic acid sequence is one whose gene expression is to be determined. The sequence-specific primer 30 can be any length that permits amplification of the desired nucleic acid molecule. In particular examples, a sequence-specific primer 30 is at least six nucleotides, such as at least 9, at least 10, at least 12, at least 15, at least 20, at least 25, at least 30, at least 35, at least 40, or at least 50 nucleotides. In particular examples the sequence-specific primer is between 6 and 100, 9 and 50, or 9 and 20 nucleotides.

In particular examples the PET tag includes the sequence 5'-$X_1X_{2(a)}X_3X_{4(a)}G_x$-3' (SEQ ID NO: 1), wherein $X_1$ is the 5'-end nucleotide of the PET tag and includes a detectable label (12, FIGS. 1A and B and FIG. 2), wherein $X_2$ and $X_4$ (20, FIG. 2) include the nucleotide sequences of length a of sufficient complementarity to form the stem of the stem-loop structure, wherein $X_3$ (22, FIGS. 1 A and B and FIG. 2) includes the loop of the stem-loop structure, wherein $G_x$ (24, FIGS. 1A and B and FIG. 2) includes the at least two consecutive G nucleotides such as 2, 3, 4, 5, or 6 nucleotides. In another example, a PET tag includes the sequence 5'-$X_1X_{2(a)}X_3X_{4(a)}G_xX_{5(n)}$-3' (SEQ ID NO: 2), wherein $X_5$ (26, FIGS. 1B and 3B) is 0 or more nucleotides such as 0, 1, 2, 3, 4, 5, 10, 15, 20, 25, 30, or 35 nucleotides. In other embodiments, $X_5$ is 1 or more nucleotides. In another example, a PET tag includes the sequence 5'-$X_1X_{2(a)}X_3X_{4(a)}$-3' (SEQ ID NO: 3), wherein $G_x$ of the PET tag (24, FIGS. 3A and B) is the 5'-nucleotides of the sequence specific primer 30 instead part of the PET tag attached to the sequence specific primer 30.

In particular examples, $X_1$ is any nucleotide, such as A, C, T, or G or any modification or nucleotide analog known to a person skilled in the art. In other examples, $X_1$ is any nucleotide except for G, such as A, C, T, or any modification or nucleotide analog thereof known to a person skilled in the art. In other examples, $X_1$ is A, C, or T. In particular examples, a is 3 or more nucleotides such as 3, 4, 5, 6, 7, 8, 9, or 10 nucleotides. In other specific examples, the sequence defined by $X_{2(a)}$ and $X_{4(a)}$ possess at least 50% complementarity to one another such as at least 50%, 60%, 70%, 80%, or 90% or 95% complementarity. In other specific examples, the sequences defined by $X_{2(a)}$ and $X_{4(a)}$ are 100% complementary to one another. In particular examples, $X_3$ is at least 3 nucleotides such as 3, 4, 5, 6, 7, 8, 9, or 10 nucleotides. In other particular examples, the nucleotides represented by $X_3$ do not include C or G. In other particular examples $X_3$ is a trinucleotide sequence, for example TAA, ATA, AAT, TTA, TAT, ATT, TTT or AAA.

In a specific example, the PET tag is 5'-TAMRA-AGGCG-CATAGCGCCTGG-3' (SEQ ID NO: 4). One skilled in the art will appreciate that TAMRA can be replaced with another fluorophore. Other exemplary PET tags are provided in the examples below.

Kits

The present disclosure provides kits that include one or more PET tags, such as a PET tag ligated or otherwise attached to a sequence-specific primer. For example, the kit can include one or more (such as two or more, for example, 2, 3, 4, 5, or 6) labeled sequence-specific primers that include a PET tag generated using the methods provided herein.

In some examples, the kits further include ligase, for example to permit ligation of a PET tag to the 5' end of a forward or a reverse target sequence-specific primer, thereby generating a PET primer.

In some examples, the kits include one or more forward or reverse target sequence-specific primers, such as forward and reverse primers that recognize a specific pathogen or a specific nucleic acid sequence whose expression is changed in response to a disorder. For example, the kit can include forward and reverse primers that can be used to amplify the nucleic acid sequence of a particular pathogen, such as a viral, bacterial, parasitic, or fungal target nucleic acid sequence. In one example, the forward and reverse primers can be used to amplify a particular human nucleic acid sequence, such target nucleic acid sequences can be associated with a disease, such as cancer. In some examples, the PET tag in the kit is already attached to the 5'-end of the forward or reverse primer. In other examples, the PET tag in the kit is separate from the forward or reverse primer, and can be ligated to the forward or reverse primer by a user.

Kits can also include other reagents, such as those used for PCR amplification. Examples include buffers, dNTPs, polymerase, and combinations thereof. In one example, kits include reagents for detection of a label on the PET tag, such as a chemiluminescent detection reagent.

The components of the kit can be present in separate, labeled containers.

Methods of Nucleic Acid Detection

The disclosed PET nucleic acid molecules and labeled sequence-specific primers can be used in any nucleic acid amplification reaction to determine whether a particular target nucleic acid sequence is present, such as a DNA or RNA molecule. For example, methods are disclosed for detecting a target nucleic acid molecule. In particular examples, the method includes incubating a sample containing nucleic acids with a PET tag attached to a forward or a reverse target sequence-specific primer (referred to herein as a PET primer), and with a corresponding forward or reverse target sequence-specific primer which does not contain the PET tag. In other examples, both the forward and the reverse target sequence contain a PET tag. The PET tag associated with the sequence-specific forward and reverse primer may be the same or different. In some examples, the sequences of the PET tag associated with the sequence-specific forward and reverse primer is the same, but the label on each is different. As described above, the 3'-end of the PET tag can be ligated to the 5'-end of the forward or reverse sequence-specific primer (e.g., see FIGS. 3A and B).

In a particular example, the sample, a forward primer containing a PET tag, and a reverse primer not containing a PET tag, or a forward primer not containing a PET tag and a reverse primer containing a PET tag, are incubated under conditions sufficient to permit amplification of the target nucleic acid. For example, the reaction can include dNTPs, polymerase, and $MgCl_2$.

Any primer extension amplification method can be used, and such methods are well known in the art. Particular examples include, but are not limited to: real-time PCR (for example see Mackay, *Clin. Microbiol. Infect.* 10(3):190-212, 2004), Strand Displacement Amplification (SDA) (for example see Jolley and Nasir, *Comb. Chem. High Throughput Screen.* 6(3):235-44, 2003), self-sustained sequence replication reaction (3SR) (for example see Mueller et al., *Histochem. Cell. Biol.* 108(4-5):431-7, 1997), ligase chain reaction (LCR) (for example see Laffler et al., *Ann. Biol. Clin. (Paris)*.51(9):821-6, 1993), or transcription mediated amplification (TMA) (for example see Prince et al., *J. Viral Hepat.* 11(3):236-42, 2004), An increase in detectable signal from the label on the labeled PET primer is monitored, wherein a significant increase in signal indicates the presence of the target nucleic acid sequence, and wherein no significant increase in signal indicates that the target nucleic acid molecule is not present in the sample. The increase in detectable signal can be monitored by any instrument that can detect the detectable signal. In particular examples, the instrument that can detect the detectable signal can be a spectrophotometer. In other particular examples, the instrument that can detect the detectable signal can be a real-time PCR thermocycler. The increase in signal can be compared to a control, such as a signal present at an earlier time-point, such as prior to nucleic acid amplification. In some examples, the increase is relative to a negative control, such as a sample known not to contain the target DNA or a sample incubated with primers that are unlabeled. In some examples, the increase is relative to a known value or range of values expected in the absence of the target sequence. In comparison to the control signal, the increase can be at least 10%, at least 20%, at least 30%, at least 40%, at least 50% at least 60%, at least 70%, at least 80%, at least 90%, at least 100%, at least 200% at least 1000% or greater increase. The detectable signal increases in a predictable manner that permits determination of whether or not a target nucleic acid sequence is present in a sample. In some examples, the increase in detectable signal allows for quantification of an amount of target nucleic acid sequence present in a sample.

For example, when the label is a fluorophore that can be quenched in a predictable manner by being in proximity to the at least two consecutive G nucleotides at the 3'-end of the PET tag (or the first two 5'-nucleotides of the sequence-specific primer), an increase in fluorescent signal during nucleic acid amplification indicates the presence of the target nucleic acid sequence in the sample, while no significant increase in fluorescent signal during nucleic acid amplification indicates that the target nucleic acid sequence is not present in the sample.

In some examples, the increase in signal is monitored during the amplification reaction, for example in real time as the amplicons are formed. For example, the detectable signal from the 5'-end label present on the PET tag is quenched when the amplification primers are freely floating in the nucleic acid amplification reaction mixture. During nucleic acid amplification, when the polymerase synthesizes nucleic acid amplicons, the primer, including the labeled PET tag, is incorporated into the amplicon and the stem-loop of the PET tag is denatured, removing the 5'-end label from proximity with the at least two consecutive G nucleotides (that is, the distance between label and G nucleotides is increased). Thus, the signal from the label will increase as it becomes incorporated into the double-stranded amplicon molecule. As more amplicons are produced during nucleic acid amplification, the signal of the reaction mixture will increase. The increase in signal can be monitored using any commercially available system. This increase in signal permits detection of a target nucleic acid sequence in the reaction.

In one example where the label is a fluorophore, the increase in signal monitored during the amplification reaction is an increase in fluorescence. The fluorescence of the fluorophore is quenched when the primers are freely floating in the nucleic acid amplification reaction mixture. During nucleic acid amplification, when polymerase synthesizes nucleic acid amplicons, the primer, including the labeled PET tag, is incorporated into the amplicon. The fluorescence of the incorporated primer increases several-fold due to dequenching of the detectable signal by its incorporation into the double-stranded amplicon molecule and movement out of proximity with the at least two consecutive Gs in the PET tag. As more amplicons are produced during nucleic acid amplification, the overall fluorescence of the reaction mixture increases. The increase in fluorescence can be measured and observed, for example by using a commercially available nucleic acid amplification system capable of measuring fluorescence (such as real-time PCR thermocyclers). An increase in fluorescent signal indicates the presence of a target nucleic acid sequence in the reaction.

Target nucleic acid molecules can be detected after nucleic acid amplification. For example, the methods can include incubating a sample containing or thought to contain the target nucleic acid molecule with a forward primer and a reverse primer that are specific for the target nucleic acid molecule. Either the forward primer or the reverse primer is linked at its 5'-end to the 3'-end of a PET tag under conditions sufficient to allow amplification of the target nucleic acid molecule (such as real-time PCR conditions). However, in some examples, both the forward and the reverse primer are linked at their 5'-ends to the 3'-end of a PET tag. The amplification results in the generation of labeled amplicons. Each amplicon is exposed to conditions that permit denaturation of the amplicon into single-stranded nucleic acid molecules, and then exposed to conditions that permit rehybridization of the strands. During each cycle of amplicon synthesis, the resulting PET primer is incorporated into a double-stranded nucleic acid molecule, denaturing the stem-loop structure of the PET tag. This results in an increase in detectable signal, for example relative to the detectable signal from the label before the formation of double-stranded DNA. An increase in signal indicates that the target nucleic acid molecule is present in the sample, and no significant change in signal indicates that the target nucleic acid molecule is not present in the sample.

In particular examples, PET primers can be used to detect multiple target nucleic acids, for example in a single reaction. In such examples, a plurality of PET tags can be ligated to the 5'-end of a plurality of target-specific forward and/or reverse primers. The 5'-end labels in such examples can be fluorescent labels that each emit a fluorescent signal at different wavelengths such that the presence of a plurality of target nucleic acids can be detected. For example, for target sequence 1, a PET-forward primer can be labeled with HEX, and for target sequence 2 a PET-forward primer can be labeled with 6-FAM, such that increase in HEX indicates the presence of target sequence 1, while an increase in 6-FAM signal indicates the presence of target sequence 2. In particular examples, the presence of multiple target nucleic acids can be monitored in real time as in real-time PCR, for example in one or more amplification reactions.

In addition to determining whether a particular target nucleic acid molecule is present, the method can further include quantifying the target nucleic acid molecule. In one example quantification includes comparing a signal to a reference value. Exemplary reference values include an expected amount of signal from a known amount of nucleic acid.

In other or additional examples, the change (e.g., increase or decrease) in signal is monitored after the amplification, for example by exposing the resulting amplicons to a melting procedure to denature the double-stranded amplicons. During the denaturation, a change in signal is detected. The resulting signals, such as decreasing fluorescence (see FIG. 8), can indicate polymorphisms in the nucleic acid amplicons. Therefore, melting curve analysis can be used to confirm the presence of a target nucleic acid sequence, and can also be used to distinguish polymorphisms in amplicons.

Samples containing nucleic acid molecules can be obtained from any appropriate specimen, for instance blood or blood-fractions (such as serum). Techniques for acquisition of such samples are well known in the art (for example see Schluger et al. *J. Exp. Med.* 176:1327-33, 1992, for the collection of serum samples). Serum or other blood fractions can be prepared in the conventional manner. For example, about 200 µL of serum can be used for the extraction of DNA for use in amplification reactions. In some examples, RNA is extracted and used in an amplification reaction (such as reverse-transcriptase PCR). Commercially available kits can also be used to obtain nucleic acid molecules from a biological sample prior to amplification.

Once a sample has been obtained, the sample can be used directly, concentrated (for example by centrifugation or filtration), purified, or combinations thereof. In one example, DNA is prepared from the sample, yielding a nucleotide preparation that is accessible to, and amenable to, nucleic acid amplification. Similarly, RNA can be prepared using a commercially available kit (such as the RNeasy Mini Kit, Qiagen, Valencia, Calif.).

Example 1

Comparison of PET Tag to TaqMan® Primers

This example describes methods used to compare the TaqMan® assay to the method of the present disclosure which uses the disclosed PET tags and primers. *Cryptosporidium parvum* was used as a model system; however one skilled in the art will appreciate that similar methods can be used to amplify any target nucleic acid molecule of interest using the disclosed PET nucleic acid molecules.

The primers were prepared as follows. Oligonucleotide primers were synthesized on automated DNA synthesizers (Applied Biosystems, Foster City Calif.) utilizing standard phosphoramidite chemistry. The PET tag of SEQ ID NO: 4 does not show any homology to *Cryptosporidium* spp. sequences. TAMRA (NNN'N'-tetramethyl-6-carboxyrhodamine) was added to the 5'-end of the oligo during synthesis using a C6-TAMRA-dT phosphoramidite (Glen Research, Sterling Va.) to produce the end labeled primer of sequence 5'TAMRA-AGGCGCATAGCGCCTGG 3' (SEQ ID NO: 4). For target specific nucleic acid amplification and detection, the TAMRA-end labeled PET tag was ligated to the 5'-end of the sequence-specific reverse primer CryJVR: 5'-ATTCCCCGTTACCCGTCA-3' (SEQ ID NO: 5) to produce PET-CryJVR. Also used in nucleic acid amplification was forward primer CryJVF: 5'-GGTGACTCAT-AATAACTTTACGGAT-3' (SEQ ID NO: 6). Both forward and reverse sequence-specific primers correspond to *C. parvum* 18S ss rRNA sequence (GenBank Accession # AY458612).

A stock of *C. parvum* oocysts contained $6 \times 10^8$ oocysts/mL. The titers of *C. parvum* oocysts stocks were determined based on hemocytometer microscopy counts. DNA was extracted using a standard nucleic acid extraction method and the resulting DNA was serially diluted and stored at −70° C. until use. Standard curves were generated using $10^3$ to $10^{-2}$ oocysts. For generation of standard curves, the crossing threshold (CT) (i.e., cycle threshold) values were plotted (y-axis) against the logarithm of the input copy numbers (x-axis). Appropriate negative controls were included in each run. To assess the log-linear relationship of the assays, the linear regression and regression coefficients ($R^2$) were calculated. The oocyst numbers do not correspond to the exact number of RNA molecules for 18S, since each oocyst contains 20 copies of 18S ssrRNA gene.

Real-time PCR amplification was carried out using the iCycler iQ4® (Bio-Rad, California, USA) platform. The reaction mixture contained primers at concentrations of 250 nM of each forward and reverse primer, 2 μl of DNA, 10 μl of 2× QuantiTect® Probe PCR kit Master Mix (Qiagen, Valencia, Calif.), and nuclease-free water to a final volume of 20 μl. The amplification reaction consisted of a hot start step at 95° C. for 15 minutes to activate the HotStarTaq® DNA polymerase. This was followed by forty five cycles of amplification including denaturation at 95° C. for 10 seconds and annealing/extension at 60° C. for 40 seconds. Fluorescence signals were collected at the end of the annealing step in channel 2 (Excitation 555 nm/Emission 576 nm).

For the TaqMan® assay, the primers and probe used are listed in Table 1. The TaqMan® probe was labeled with FAM (6-Carboxy-fluorescein) at the 5'-end and with Black Hole Quencher® dye at the 3'-end (CDC Biotechnology Core Facility, Atlanta, Ga.). Amplifications were carried out using the iCycler iQ4® platform (Bio-Rad, California, USA) for a total of 45 cycles. For TaqMan® PCR, the 20 μl reaction contained 10 μl of 2× QuantiTect® Probe PCR kit Master Mix (Qiagen, Valencia, Calif.), 2 μl of DNA, and primers and probe at concentrations of 250 and 100 nM respectively. Prior to amplification, denaturation was carried out at 95° C. for 15 minutes, followed by 45 PCR cycles at 95° C. (10 seconds) and annealing/extension at 60° C. for 40 seconds. Fluorescence signals were collected at the end of the annealing step in channel 1 (490 nm).

TABLE 1

Sequences used in the TaqMan ® real-time PCR assay

| Primer or probe | Sequence (5'-3') | Position* | SEQ ID No. |
|---|---|---|---|
| | | 18S ssrRNA* | |
| JVAF (forward) | ATGACGGGTAACGGGGAAT | 100-118 | 7 |
| JVAR (Reverse) | CCAATTACAAAACCAAAAA GTCC | 258-236 | 8 |
| JVAP (Probe) | FAM-CGCGCCTGCTGCCTT CCTTAGATG-BHQ | 161-185 | 9 |

*Position based on GenBank accession #AY458612 for 18S small subunit ribosomal RNA gene.

Slopes, regression coefficients, and PCR amplification efficiency curves for both PET primer and TaqMan® probe assays were calculated using iCycler iQ® software; efficiency (E) was calculated according to the equation $E=10^{(-1/slope)}$.

Figure 4:
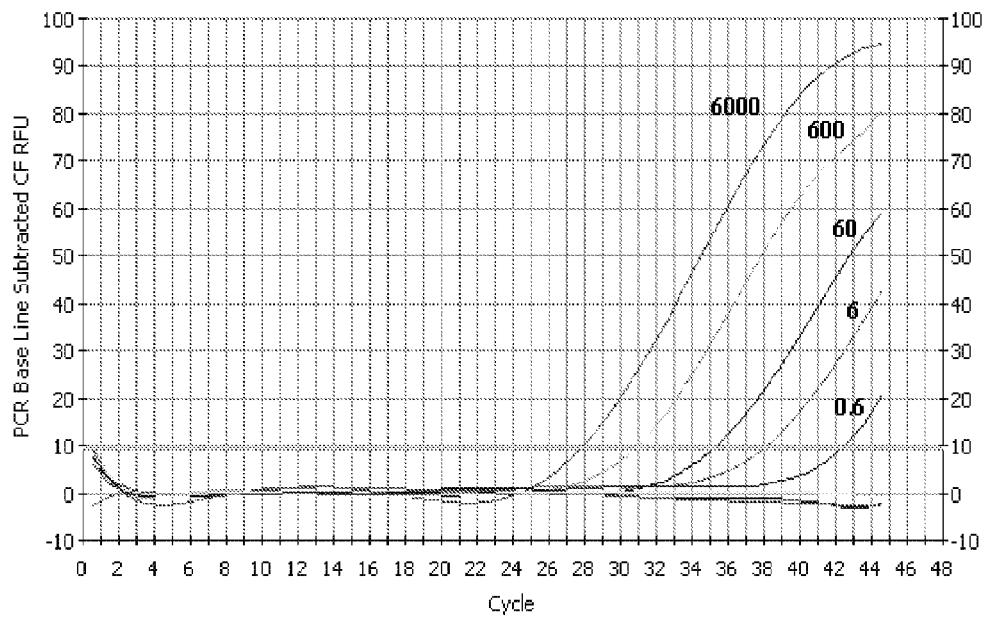
FIG. 4 is a graph of the quantitative PET PCR assay.
Figure 5:
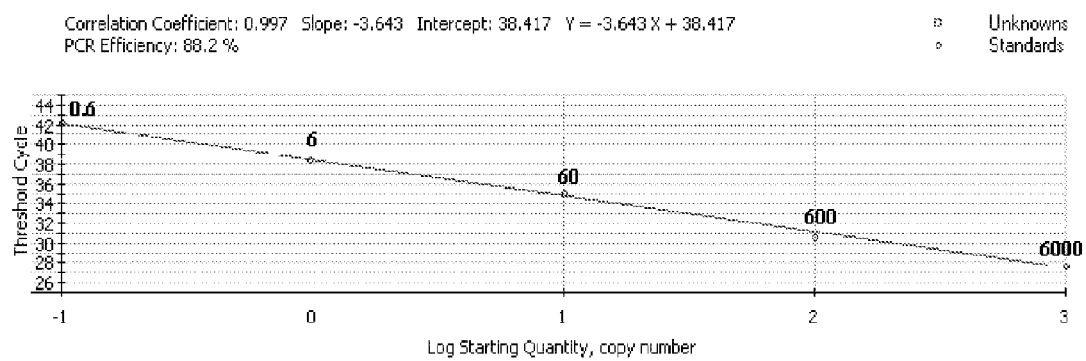
FIG. 5 is a logarithmic plot of the PET PCR assay data.
Figure 6:
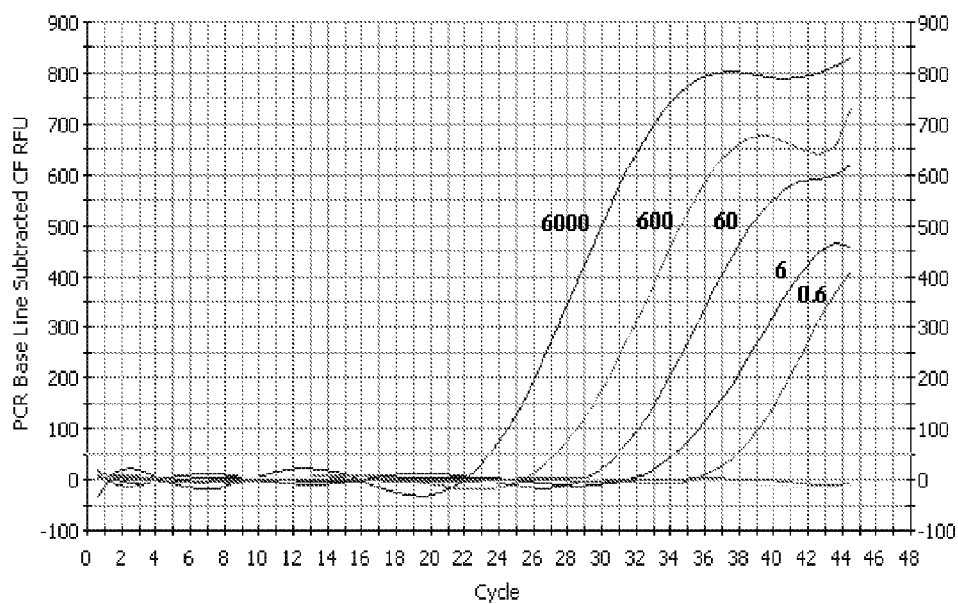
FIG. 6 is a graph of the TaqMan™ comparison assay.
Figure 7:
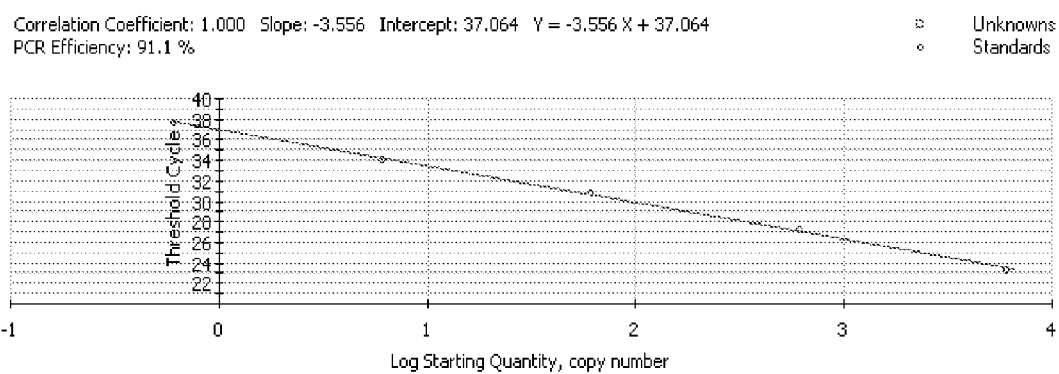
FIG. 7 is a logarithmic plot of the TaqMan™ comparison assay data.

As shown in FIG. 4, nucleic acid amplification with the disclosed PET PCR assay demonstrates a dynamic range of detection from 6000 oocysts to 0.6 oocysts per PCR reaction. As shown in FIG. 5, the logarithmic plot of this data presents the relationship between the concentration of DNA and CT values. As shown in FIG. 6, the TaqMan® assay exhibits similar sensitivity as the PET primer assay in nucleic acid amplification for a dynamic range of detection from 6000 oocysts to 0.6 oocysts per PCR reaction. Likewise, in FIG. 7 the logarithmic plot of this data presents a similar relationship between the concentration of DNA and CT values in comparison to the PET PCR assay. In both detection methods the same level of sensitivity was achieved. A seed level of 0.06 oocysts was not detected by either method.

Example 2

Melting Curve Analysis to Detect Polymorphisms

This example describes methods used to detect polymorphisms using the disclosed PET tags. Similar methods can be used to detect any target nucleic acid molecule of interest using the disclosed PET nucleic acid molecules.

Melting curve analysis of PET primer assay products was performed after amplification (as described in Example 1), and consisted of 1 minute at 95° C., followed by 1 minute at 55° C., and 80 10 second steps with a 0.5° C. increase in temperature at each step. Threshold values for threshold cycle determination were generated automatically by the iCycler iQ® software.

Figure 8:
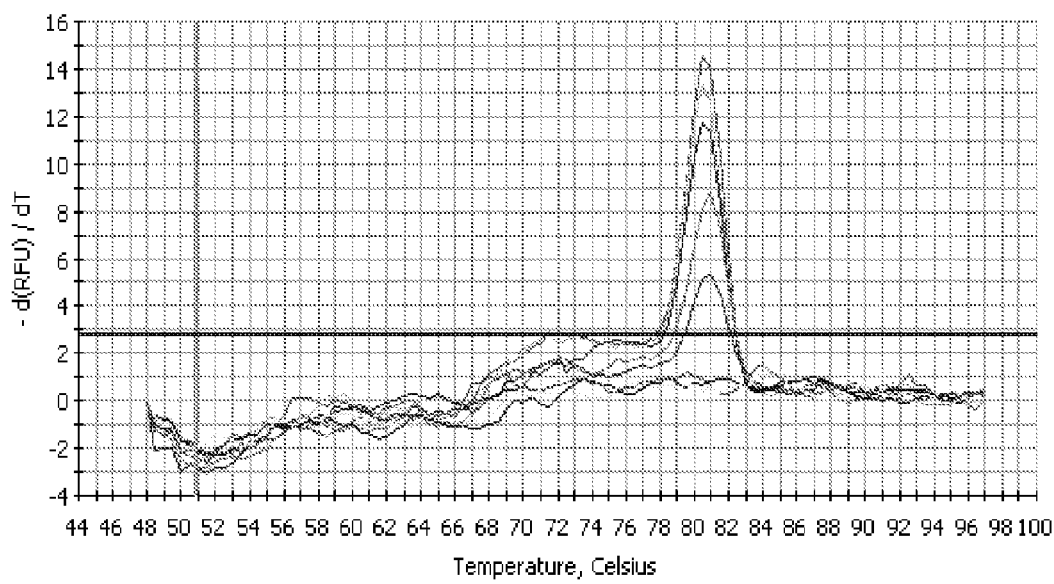
FIG. 8 is a graph of a melting curve analysis of the PET PCR amplification products.

Lack of variation in PCR products and the absence of primer dimers were ascertained from the melt curve profile of the PCR products. The melting temperature (Tm) for each sample was used to verify the specificity of the real-time plot. As shown in FIG. 8, the melting curve analysis for the PET PCR assay of the 18S ssrRNA gene target at different concentrations (as in Example 1) confirms the specificity of the PET primers.

Example 3

Exemplary PET Tags

This example provides an additional 18 exemplary PET tags. Although the primers shown in Table 2 include target-specific sequences for the *C. parvum* 18S ssrRNA gene, one skilled in the art will appreciate that the target-specific portion of SEQ ID NOS: 10-27 (underlined portion in Table 2), can be replaced with other desired target-specific sequences. That is, the PET tags in Table 2 (non-underlined portion) can be used with other desired target-specific sequence primers.

Table 2 shows labeled target-specific sequences that include a PET tag portion (not underlined) and a target specific portion (underlined). These primers include different numbers of nucleotides in the loop (e.g., 16 of FIG. 2) and different numbers of consecutive Gs (e.g., 24 of FIG. 2). These primers were evaluated for their ability to amplify a *C. parvum* 18S ssrRNA target sequence as described in Example 1 and melting cure analysis was performed as described in Example 2. The forward primers in Table 2 were used with reverse primer CryJVR: 5'-ATTCCCCGTTACCCGTCA-3' (SEQ ID NO: 5).

TABLE 2

Labeled target-specific primers

| SEQ ID # | # nt in loop | G or C-position | Hairpin kcal/mol | Sequence* | Amplification | melt |
|---|---|---|---|---|---|---|
| 10 | 3 | AGG-GG | dG-14 | AGGCGCGATACGCGCCTGGACTCA<br>TAATAACTTTACGGAT<br>*AGGCGCGATCACGCGCCTGGACTC* | Yes | Yes |
| 11 | 4 | AGG-GG | dG-14 | ATAATAACTTTACGGAT<br>*AGGCGCGATTCACGCGCCTGGGGA* | Yes | Yes |
| 12 | 5 | AGG-GGGG | dG-14 | CTCATAATAACTTTACGGAT<br>*ACCCGCGATACGCGGGTGGACTCA* | Yes | Yes |
| 13 | 3 | ACCC-GG | dG-14 | TAATAACTTTACGGAT<br>*ACCCGCGATACCGCGGGTGGACTC* | Yes | No |
| 14 | 4 | ACCC-GG | dG-14 | ATAATAACTTTACGGAT<br>*ACCCGCGATAACCGCGGGTGGGGA* | Yes | No |
| 15 | 5 | ACCC-GGGG | dG-14 | CTCATAATAACTTTACGGAT<br>*ACCGCGATACGCGGTGGACTCATA* | Yes | No |
| 16 | 3 | ACC-GG | dG-11 | ATAACTTTACGGAT<br>*ACCGCGATCACGCGGTGGACTCAT* | Yes | No |
| 17 | 4 | ACC-GG | dG-11 | AATAACTTTACGGAT<br>*ACCGCGATTCACGCGGTGGACTCA* | Yes | No |
| 18 | 5 | ACC-GG | dG-11 | TAATAACTTTACGGAT<br>*ACCGCATAGCGGTGGACTCATAAT* | Yes | No |
| 19 | 3 | ACC-GG | dG-7 | AACTTTACGGAT<br>*ACCGCATCAGCGGTGGACTCATAA* | Yes | No |
| 20 | 4 | ACC-GG | dG-7 | TAACTTTACGGAT<br>*ACCGCATTCAGCGGTGGACTCATA* | Yes | No |
| 21 | 5 | ACC-GG | dG-7 | ATAACTTTACGGAT<br>*AGGCGCATAGCGCCTGGACTCATA* | Yes | No |
| 22 | 3 | AGG-GG | dG-11 | ATAACTTTACGGAT<br>*AGGCGATACGCCTGGACTCATAAT* | Yes | Yes |
| 23 | 3 | AGG-GG | dG-8 | AACTTTACGGAT<br>*AGGCGCATCAGCGCCTGGACTCAT* | Yes | Yes |
| 24 | 4 | AGG-GG | dG-11 | AATAACTTTACGGAT<br>*AGGCGATCACGCCTGGACTCATAA* | Yes | Yes |
| 25 | 4 | AGG-GG | dG-8 | TAACTTTACGGAT<br>*AGGCGCATTCAGCGCCTGGACTCA* | Yes | Yes |
| 26 | 5 | AGG-GG | dG-11 | TAATAACTTTACGGAT<br>*AGGCGATTCACGCCTGGACTCATA* | Yes | Yes |
| 27 | 5 | AGG-GG | dG-8 | ATAACTTTACGGAT | Yes | Yes |

*Italicized letters represent the stem-loop portion of the PET Tag (e.g., 16 of FIG. 2);
Gs in bold are overhang nucleotides (e.g., 24 of FIG. 2); underlined sequence is complimentary
to the target DNA sequence (e.g., 30 of FIG. 3); primers are labeled with FAM at the 5'-A.

As shown in Table 2, all of the primers were able to detect target sequences using amplification. However, primers with 5'-ACC (instead of 5'-AGG) at the 5'-end can also be used in amplification of target but did not have the benefit of melting curve analysis. When the fluorescently labeled 5'-A comes into proximity to GG is quenched initially and quenching effect reduced when the complimentary CC's are synthesized. Other parameters that influence the sensitivity of the assay included delta G (expressed as –kcal/mol) of the loop and number of nucleotides in loop. In some examples, at least three nucleotides are required to form the loop of the stem loop structure. Although the loop size can be increased, this is generally avoided to reduce production costs.

Example 4

Effect of Additional G Nucleotides on 3'-End of Universal Tag

This example describes methods used to determine the effect on fluorescence on changing the number of Gs at the 3'-end of the PET primer.

The PET tag 5'-FAM-AGGX$_{(1)}$X$_{(2)}$X$_{(3)}$ATAX$_{(4)}$X$_{(5)}$X$_{(6)}$CCTG(n) (SEQ ID NO: 28) was used to alter the number of Gs at G(n) on the 3'-end, wherein X$_{(1)}$ is complementary to X$_{(6)}$, X$_{(2)}$ is complementary to X$_{(5)}$, and X$_{(3)}$ is complementary to X$_{(4)}$. In a specific example the PET tag was 5'-FAM- AGGCGCATAGCGCCTX$_{(1)}$ (SEQ ID NO: 29), wherein X$_{(1)}$ is zero to two G residues. The following primers were used:

```
#1: No 3'-end Gs, forward PET-tagged sequence
specific primer was
                                     SEQ ID NO: 30;
5'-FAM-AGGCGCATAGCGCCTATGACGGGTAACGGGGAAT;

#2-one 3'-end G, forward PET-tagged sequence
specific primer was
                                     SEQ ID NO: 31;
5'-FAM-AGGCGCATAGCGCCTGATGACGGGTAACGGGGAAT;
and

#3-two 3'-end Gs, forward PET-tagged sequence
specific primer was
                                     SEQ ID NO: 32.
5'-FAM-AGGCGCATAGCGCCTGGATGACGGGTAACGGGGAAT;
```

The underlined portions of the PET primers are the target sequence-specific primer sequences (non-underlined portion is the PET tag). All of these forward PET primers were used with reverse sequence-specific primer CCAATTACAAAAC-CAAAAAGTCC (SEQ ID NO: 33) to amplify *C. parvum* DNA within the 18S ssrRNA gene as follows. The target DNA was detected with the forward and reverse primers described above. The forward primer was labeled with FAM at the 5'-end. DNA was extracted from *C. parvum* oocysts and suspended in 80 µl Tris EDTA (TE, pH 8.0) buffer. Two microliters of DNA were added per reaction. The amplification reaction mixture consisted of Quantifast Probe PCR with no ROX vial kit reaction mixture (cat#204354—Qiagen), FAM-labeled PET forward primer and reverse primer (0.25 µM each). An aliquot (2 µl) of the extracted DNA sample was added to the PCR 96 well-plate containing 18 µl reaction mixture along with appropriate negative control were included in each experiment. The protocol took approximately 60 minutes to complete with the following PCR conditions: hot-start denaturation step at 95° C. for 3 minutes, followed by 45 cycles with a 95° C. denaturation for 10 seconds, 60° C. annealing for 50 seconds with single fluorescence acquisition in FAM™ dye, HEX™ dye and Cy5® dye channels on a real-time PCR instrument (7500 Real-time PCR system). A positive result was recorded for FAM.

Figure 9:
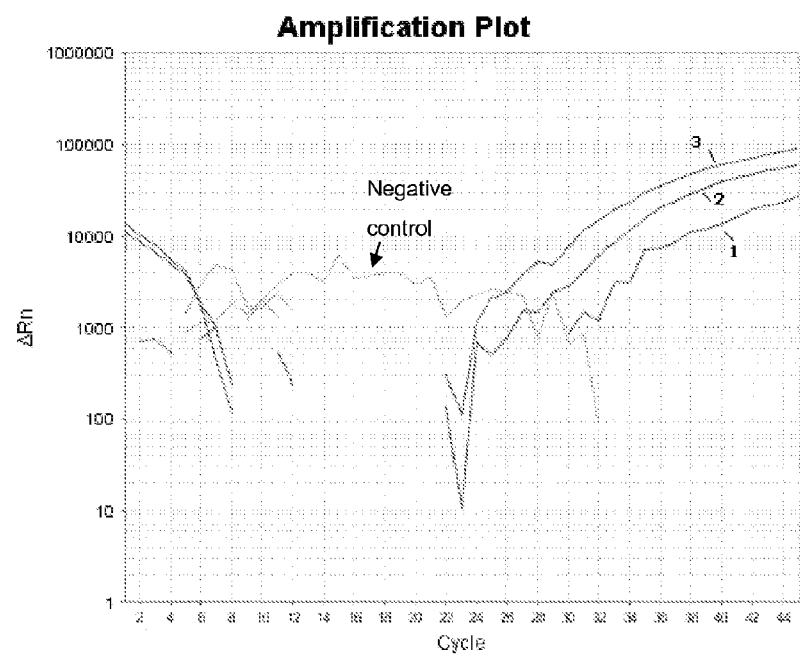
FIG. 9 is a graph showing an increase in detectable FAM signal during amplification of a target sequence using PET primers containing different numbers of Gs at the 3'-end of the PET tag (1=no Gs, 2=1 G, 3=2 Gs).

Traces for each of the three reactions with zero 3'-end Gs (#1), one 3'-end G (#2), or two 3'-end Gs (#3) is shown in FIG. 9. As shown in FIG. 9, as the number of 3'-end G's increases from zero to two, the CT value decreases from approximately 38 (curve #1) to 34 (curve #2) to 31 (curve #3). Thus the resulting amplicons can be detected at an earlier cycle number. Even without a G at the 3'-end, there is still an increase in fluorescence due to the production of amplicons. This is because during the hairpin folding stage the fluorescently-labeled nucleotide is sandwiched between 2G's on either side and even if there are no G's on one side, the two G's on the other side quenches the fluorophore Example 5

Use of PET Primer in a Multiplex Format

This example describes methods used to demonstrate that PET primers can be used in multiplex reactions.

The target DNA was detected with a forward and a reverse primer labeled either with FAM or HEX at 5'-end, and a specific probe labeled with Quasar® 670 dye. DNA was extracted from *C. parvum* oocysts then suspended in 80 µl Tris EDTA (TE, pH 8.0) buffer. Two microliters of DNA were added per reaction. The amplification reaction mixture consisted of Quantifast® Probe PCR kit reaction mixture with no ROX (cat#204354—Qiagen), with one of the following primer/probe sets:

```
#1: FAM-labeled forward primer
                                     (SEQ ID NO: 34)
5'-FAM-AGGCGGATACCGCCTGGATGACGGGTAACGGGGAAT, HEX-labeled reverse primer
                                     (SEQ ID NO: 35)
5'-HEX-AGGCGGATACCGCCTGGCCAATTACAAAACCAAAAAGTCC (0.25 µM each) and Quas670 probe (0.2 µM)

(Quas670-CGCGCCTGCTGCCTTCCTTAGATG-BHQ3;
SEQ ID NO: 36);
or

#2: HEX-labeled forward primer
                                     (SEQ ID NO: 37)
5'-HEX-AGGCGGATACCGCCTGGATGACGGGTAACGGGGAAT, FAM-labeled reverse primer
                                     (SEQ ID NO: 38)
5'-FAM-AGGCGGATACCGCCTGGCCAATTACAAAACCAAAAAGTCC (0.25 µM each) and Quas670 probe (0.2 µM;
SEQ ID NO: 36)
```

The underlined portions of the PET primers are the target sequence-specific primer sequences (non-underlined portion is the PET tag). An aliquot (2 µl) of the extracted DNA sample was added to the PCR 96 well-plate containing 18 µl reaction mixture along with appropriate negative control were included in each experiment. The protocol took approximately 30 minutes to complete with the following PCR conditions: hot-start denaturation step at 95° C. for 3 minutes, followed by 45 cycles with a 95° C. denaturation for 10 seconds, 60° C. annealing for 50 seconds with single fluorescence acquisition in FAM™ dye, HEX™ dye and Cy5® dye channels on a real-time PCR instrument (7500 Real-time PCR system). A positive result was recorded for FAM™ dye, HEX™ dye and Cy5® dye channels.

Figure 10A:
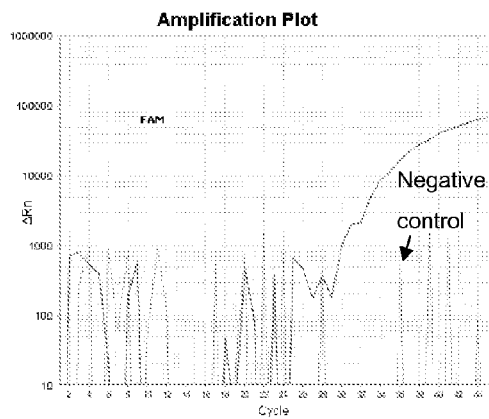
FIGS. 10A and 10B are graphs showing an increase in detectable (A) FAM and (B) HEX signal during amplification of a target sequence using (A) FAM-labeled PET tags attached to the forward primer and (B) HEX-labeled PET tags attached to the reverse primer. A Cy5® dye-labeled TaqMan® probe was used in these reactions, but the fluorescence data is shown in FIG. 10E.
Figure 10B:
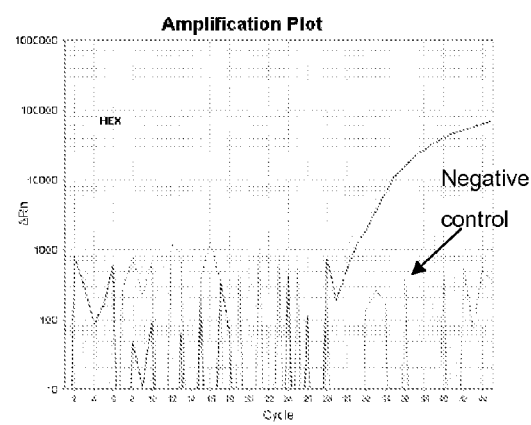
Figure 10C:
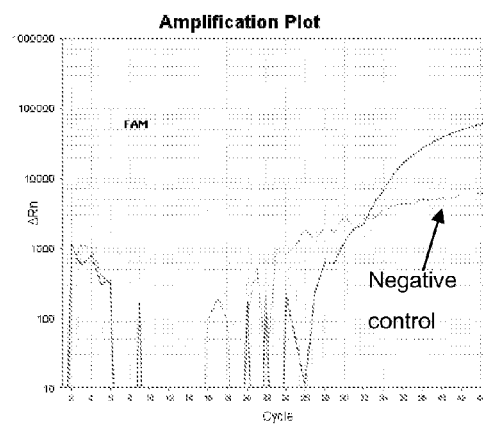
FIGS. 10C and 10D are graphs showing an increase in detectable (C) FAM and (D) HEX signal during amplification of a target sequence using FAM-labeled PET tags attached to the reverse primer and (D) HEX-labeled PET tags attached to the forward primer. A Cy5® dye-labeled TaqMan® probe was used in these reactions, but the fluorescence data is shown in FIG. 10F.
Figure 10D:
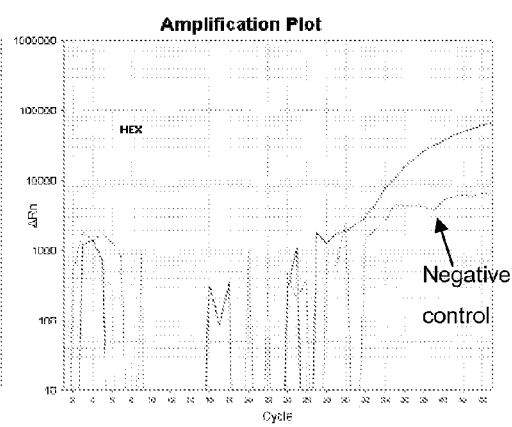
Figure 10E:
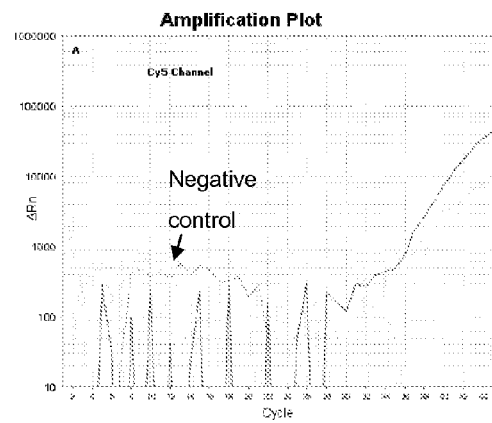
FIGS. 10E and 10F are graphs showing an increase in detectable Cy5® dye signal from TaqMan® probes during amplification of a target sequence using the (E) FAM-forward primer and HEX-reverse primer described in FIGS. 10A and 10B or (F) HEX-forward primer and FAM-reverse primer described in FIGS. 10C and 10D.
Figure 10F:
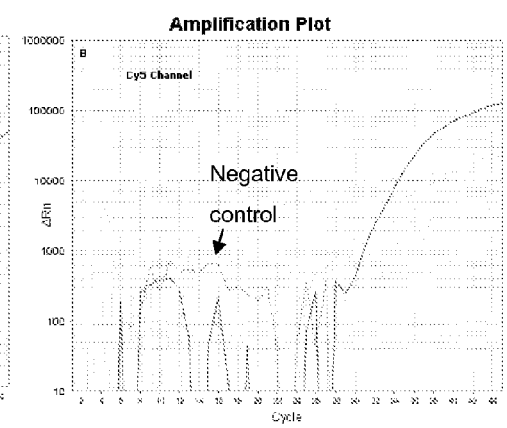

As shown in FIGS. 10A and 10B, amplification of the target *Cryptosporidium* sequence was detected using PET forward and reverse primers labeled with FAM (FIG. 10A) and HEX (FIG. 10B), respectively, as indicated by an increase in fluorescence over time. A TaqMan® probe was included in the PET primer reactions to demonstrate that signal from a labeled probe could also be obtained in conjunction with use of the PET primers. Fluorescence signal from a TaqMan® probe labeled with Quasar® 670 dye at 5'-end and BHQ3 at the 3'-end (SEQ ID NO: 36) is shown in FIG. 10E. Similar PET primer (FIGS. 10C and 10D) and TaqMan® probe (FIG. 10F) fluorescence results were obtained when the fluorophores were switched between the forward and reverse primers (FIGS. 10C and 10D).

Example 6

Use of PET Tags with an Array

This example describes methods that can be used to detect the presence of a nucleic acid molecule using the disclosed PET tags in combination with an array, such as a microarray.

In one example, the method includes amplification of a target nucleic acid sequence using a PET tag attached to the forward or reverse primer (e.g., see FIGS. 3A and B). The primer not containing a PET tag can include another label, such as a fluorophore, such as Cy3® dye or Cy5® dye. For example, real-time PCR can be performed using a forward primer labeled with a PET tag using the methods disclosed herein, and a labeled reverse primer (for example labeled with Cy3® dye or Cy5® dye). The resulting amplicons can be analyzed using the methods disclosed herein to determine if the sample analyzed is positive or negative for the target nucleic acid of interest.

The resulting PCR products (amplicons) from the positive reactions can be denatured at 100° C. for 2 minutes and chilled on ice immediately prior to hybridization to an array containing one or more nucleic acid sequence targets of interest. A particular example of such a microarray is a DNA chip. In one example, the amino group of the target nucleic acid molecule can be linked at its 5'-end to the surface of the array. If the target nucleic acid sequence is present on the array, the amplicons previously generated (which contain at least one detectable label, such as two detectable labels) will hybridize to the target nucleic acid on the array. The resulting hybridization will produce an increase in signal due to the present of the detectable label on the amplicon. For example, if one of the primers included Cy3® dye or Cy5® dye, the resulting Cy3® dye or Cy5® dye labeled product will produce an increase in fluorescence intensity, which can be detected and in some examples further quantified.

Such a method can be used to confirm the positive or negative results obtained with amplification using a PET tag disclosed herein.

Example 7

Use of Universal Tags with Pyrosequencing

This example describes methods that can be used to sequence a nucleic acid molecule using the disclosed PET tags in combination with pyrosequencing.

In one example, the method includes amplification of a target nucleic acid sequence using a PET tag attached to the 5'-end of a forward or reverse primer. The primer not containing a PET tag can include biotin at its 5'-end. The labeled forward and reverse primers are used to amplify a target nucleic acid sequence, for example by using real-time PCR methods disclosed herein. The resulting amplicons can be analyzed using the methods disclosed herein to determine if the sample analyzed is positive or negative for the target nucleic acid of interest. The resulting amplicons would contain a detectable biotin label.

The biotin labeled amplicon is separated after denaturation and adhesion of the amplicons to streptavidin-coated magnetic beads. The separated strands are then sequenced using pyrosequencing with an appropriate sequencing primer, using methods known in the art (for a review of pyrosequencing see Franca et al., *Q. Rev. Biophys.* 35(2):169-200, 2002).

Example 8

Detection of a Nucleic Acid Molecule in a Subject

This example describes methods to determine if a particular nucleic acid molecule is present, for example present in a sample obtained from a subject.

In one example, the method includes amplification of a target nucleic acid sequence from a sample using a PET tag attached to the forward or reverse primer specific for the target nucleic acid sequence. In one example, the sample is obtained from a subject infected or suspected of being infected with a pathogen, such as a virus, bacterium, parasite, fungi, or combinations thereof. In this example, the target nucleic acid sequence can be a sequence specific to the pathogen of interest, or a nucleic acid molecule of the subject whose expression is altered (such as increased or decreased) in response to the infection, or combinations thereof.

In another example, the sample is obtained from a subject having or suspected of having a disease, such as cancer. In particular examples, the subject is being treated or has been treated for the disease, and the method is used to determine the subject's response to the treatment. In this example, the target nucleic acid sequence can be a nucleic acid molecule of the subject whose expression is altered (such as increased or decreased) due to the disease, a control sequence (such as a sequence that detects expression of a housekeeping gene), or combinations thereof. Housekeeping genes are known in the art (for example see Janssens et al., *Mol. Diagn.* 8(2):107-13, 2004), and can include porphobilinogen deaminase (PBGD); mitochondrial ATP synthase 6 (mATPsy6); and glyceraldehyde-3-phosphate dehydrogenase (GAPDH). Ideally, a housekeeping gene has expression levels that remain relatively constant in different experimental conditions.

The primer not containing a PET tag can include another label, such as a fluorophore, such as Cy3® dye or Cy5® dye. For example, real-time PCR can be performed using a forward primer labeled with a PET tag using the methods disclosed herein, and an unlabeled or labeled reverse primer (for example labeled with Cy3® dye or Cy5® dye). The resulting amplicons can be analyzed using the methods disclosed herein to determine if the sample analyzed is positive or negative for the target nucleic acid of interest. If desired, the amplicons can be further analyzed, for example using an array, to confirm the amplification results. In some examples, quantification of the target nucleic acid is performed.

In view of the many possible embodiments to which the principles of the disclosure can be applied, it should be recognized that the illustrated embodiments are only examples of the disclosure and should not be taken as limiting the scope of the invention. Rather, the scope of the disclosure is defined by the following claims. We therefore claim as our invention all that comes within the scope and spirit of these claims:

We claim:

1. A method of detecting a target nucleic acid molecule, comprising:

incubating a sample comprising the target nucleic acid molecule with a forward primer comprising a sequence homologous to the target nucleic acid molecule and a reverse primer comprising a sequence homologous to the target nucleic acid molecule under conditions sufficient to allow amplification of the target nucleic acid molecule;

amplifying the target nucleic acid molecule using real-time polymerase chain reaction (PCR), thereby generating a labeled amplicon;

denaturing the labeled amplicon;

generating a melting curve; and detecting a signal from the label, wherein the forward primer or the reverse primer is linked at its 5'-end to the 3'-end of a photoinduced electron transfer (PET) tag, wherein the PET tag comprises the sequence 5'-AGGCGCATAGCGCCTGG-3' (SEQ ID NO: 4); 5'-AGGCGCGATACGCGCCTGG-3' (nucleotides 1 to 19 of SEQ ID NO: 10); 5'-AGGCGCGATCACGCGCCTGG-3' (nucleotides 1 to 20 of SEQ ID NO: 11); 5'-AGGCGCGATTCACGCGCCTGG-3' (nucleotides 1 to 21 of SEQ ID NO: 12); 5'-AGGCGATACGCCTGG-3' (nucleotides 1 to 15 of SEQ ID NO: 23); 5'-AGGCGCATCAGCGCCTGG-3' (nucleotides 1 to 18 of SEQ ID NO: 24); 5'-AGGCGATCACGCCTGG-3' (nucleotides 1 to 16 of SEQ ID NO: 25); 5'-AGGCGCATTCAGCGCCTGG-3' (nucleotides 1 to 19 of SEQ ID NO: 26); or 5'-AGGCGATTCACGCTGG-3' (nucleotides 1 to 17 of SEQ ID NO: 27), wherein the 5'-end nucleotide of the PET tag comprises a label, wherein the PET tag comprises a stem and a loop of a stem-loop, wherein the PET tag comprises two consecutive G nucleotides at the 3'-end of the PET tag, wherein the stem-loop brings the label on the 5'-end nucleotide and the two consecutive G nucleotides at the 3'-end of the PET tag into proximity, thereby quenching a detectable signal from the label in the absence of a target nucleic acid sequence, wherein the PET tag does not substantially hybridize to the target nucleic acid sequence recognized by the forward and reverse primers, and wherein the detectable signal from the label is unquenched when the labeled forward or reverse primer is incorporated into the amplicon, wherein an increase in signal detected during the real-time PCR indicates that the target nucleic acid molecule is present in the sample and wherein no significant increase in signal detected during the real-time PCR indicates that the target molecule is not present in the sample, and wherein a single peak detected during generating the melting curve indicates that the target nucleic acid molecule is present in the sample and wherein no single peak detected during generating the melting curve indicates that the target molecule is not present in the sample.

2. The method of claim 1, wherein the label is a fluorophore.

3. The method of claim 1, wherein the forward and reverse primers are at least 18 nucleotides in length.

4. The method of claim 1, wherein the 5'-end of the forward primer or the reverse primer is attached to the 3'-end of the PET tag.

5. The method of claim 1, further comprising quantifying the signal from the label.

6. The method of claim 1, wherein the forward primer is linked at its 5'-end to the 3'-end portion of the PET tag and wherein the reverse primer is not linked to the PET tag.

7. The method of claim 1, wherein the reverse primer is linked at its 5'-end to the 3'-end portion of the PET tag and wherein the forward primer is not linked to the PET tag.

8. The method of claim 1, wherein the signal from the label is detected following each primer extension cycle.

9. The method of claim 1, wherein a hairpin formed by the PET tag has a delta G (kcal/mol) value of −14 to −8.

* * * * *

SEQUENCE LISTING

```
<160> NUMBER OF SEQ ID NOS: 38

<210> SEQ ID NO 1
<211> LENGTH: 6
<212> TYPE: DNA
<213> ORGANISM: Artificial Sequence
<220> FEATURE:
<223> OTHER INFORMATION: exemplary PET tag
<220> FEATURE:
<221> NAME/KEY: misc_feature
<222> LOCATION: (1)..(1)
<223> OTHER INFORMATION: N at position 1 is a labeled nucleotide
```

```
<220> FEATURE:
<221> NAME/KEY: misc_feature
<222> LOCATION: (2)..(2)
<223> OTHER INFORMATION: N at position 2 is complementary to N at
      position 4 and forms the stem of the stem-loop structure
<220> FEATURE:
<221> NAME/KEY: misc_feature
<222> LOCATION: (3)..(3)
<223> OTHER INFORMATION: N at position 3 is the loop of the stem-loop
      structure
<220> FEATURE:
<221> NAME/KEY: misc_feature
<222> LOCATION: (4)..(4)
<223> OTHER INFORMATION: N at position 4 is complementary to N at
      position 2 and forms the stem of the stem-loop structure
<220> FEATURE:
<221> NAME/KEY: misc_feature
<222> LOCATION: (6)..(6)
<223> OTHER INFORMATION: additional "Gs" may be appended to the 3' end
      of the sequence

<400> SEQUENCE: 1 nnnngg                                                              6

<210> SEQ ID NO 2
<211> LENGTH: 7
<212> TYPE: DNA
<213> ORGANISM: Artificial Sequence
<220> FEATURE:
<223> OTHER INFORMATION: exemplary PET tag
<220> FEATURE:
<221> NAME/KEY: misc_feature
<222> LOCATION: (1)..(1)
<223> OTHER INFORMATION: N at position 1 is a labeled nucleotide
<220> FEATURE:
<221> NAME/KEY: misc_feature
<222> LOCATION: (2)..(2)
<223> OTHER INFORMATION: N at position 2 is complementary to N at
      position 4 and forms the stem of the stem loop
<220> FEATURE:
<221> NAME/KEY: misc_feature
<222> LOCATION: (3)..(3)
<223> OTHER INFORMATION: N at position 3 is the loop of the stem loop
<220> FEATURE:
<221> NAME/KEY: misc_feature
<222> LOCATION: (4)..(4)
<223> OTHER INFORMATION: N at position 4 is complementary to N at
      position 2 and forms the stem of the stem loop
<220> FEATURE:
<221> NAME/KEY: misc_feature
<222> LOCATION: (7)..(7)
<223> OTHER INFORMATION: N at position 7 is zero or more nucleotides

<400> SEQUENCE: 2 nnnnggn                                                             7

<210> SEQ ID NO 3
<211> LENGTH: 4
<212> TYPE: DNA
<213> ORGANISM: Artificial Sequence
<220> FEATURE:
<223> OTHER INFORMATION: exemplary PET tag
<220> FEATURE:
<221> NAME/KEY: misc_feature
<222> LOCATION: (1)..(1)
<223> OTHER INFORMATION: N at position 1 is a labeled nucleotide
<220> FEATURE:
<221> NAME/KEY: misc_feature
<222> LOCATION: (2)..(2)
<223> OTHER INFORMATION: N at position 2 is complementary to N at
      position 4 and forms the stem of the stem loop
<220> FEATURE:
<221> NAME/KEY: misc_feature
<222> LOCATION: (3)..(3)
<223> OTHER INFORMATION: N at position 3 is the loop of the stem loop
```

```
<220> FEATURE:
<221> NAME/KEY: misc_feature
<222> LOCATION: (4)..(4)
<223> OTHER INFORMATION: N at position 4 is complementary to N at
      position 2 and forms the stem of the stem loop

<400> SEQUENCE: 3 nnnn                                                                    4

<210> SEQ ID NO 4
<211> LENGTH: 17
<212> TYPE: DNA
<213> ORGANISM: Artificial Sequence
<220> FEATURE:
<223> OTHER INFORMATION: exemplary PET tag
<220> FEATURE:
<221> NAME/KEY: misc_feature
<222> LOCATION: (1)..(1)
<223> OTHER INFORMATION: A is labeled with TAMRA

<400> SEQUENCE: 4
aggcgcatag cgcctgg                                                     17

<210> SEQ ID NO 5
<211> LENGTH: 18
<212> TYPE: DNA
<213> ORGANISM: Artificial Sequence
<220> FEATURE:
<223> OTHER INFORMATION: reverse primer for amplifying C. parvum 18S ss
      rRNA

<400> SEQUENCE: 5
attccccgtt acccgtca                                                    18

<210> SEQ ID NO 6
<211> LENGTH: 25
<212> TYPE: DNA
<213> ORGANISM: Artificial Sequence
<220> FEATURE:
<223> OTHER INFORMATION: C. parvum 18S ss rRNA sequence-specific forward
      primer

<400> SEQUENCE: 6
ggtgactcat aataacttta cggat                                            25

<210> SEQ ID NO 7
<211> LENGTH: 19
<212> TYPE: DNA
<213> ORGANISM: Artificial Sequence
<220> FEATURE:
<223> OTHER INFORMATION: forward Taqman primer

<400> SEQUENCE: 7
atgacgggta acggggaat                                                   19

<210> SEQ ID NO 8
<211> LENGTH: 23
<212> TYPE: DNA
<213> ORGANISM: Artificial Sequence
<220> FEATURE:
<223> OTHER INFORMATION: reverse Taqman primer

<400> SEQUENCE: 8
ccaattacaa aaccaaaaag tcc                                              23

<210> SEQ ID NO 9
<211> LENGTH: 24
```

```
<212> TYPE: DNA
<213> ORGANISM: Artificial Sequence
<220> FEATURE:
<223> OTHER INFORMATION: Taqman probe
<220> FEATURE:
<221> NAME/KEY: misc_feature
<222> LOCATION: (1)..(1)
<223> OTHER INFORMATION: C is labeled with FAM
<220> FEATURE:
<221> NAME/KEY: misc_feature
<222> LOCATION: (24)..(24)
<223> OTHER INFORMATION: G is labled with BHQ

<400> SEQUENCE: 9
cgcgcctgct gccttcctta gatg                                          24

<210> SEQ ID NO 10
<211> LENGTH: 40
<212> TYPE: DNA
<213> ORGANISM: Artificial Sequence
<220> FEATURE:
<223> OTHER INFORMATION: exemplary PET primer
<220> FEATURE:
<221> NAME/KEY: misc_feature
<222> LOCATION: (1)..(19)
<223> OTHER INFORMATION: PET tag portion
<220> FEATURE:
<221> NAME/KEY: misc_feature
<222> LOCATION: (20)..(40)
<223> OTHER INFORMATION: sequence-specific primer portion

<400> SEQUENCE: 10
aggcgcgata cgcgcctgga ctcataataa ctttacggat                         40

<210> SEQ ID NO 11
<211> LENGTH: 41
<212> TYPE: DNA
<213> ORGANISM: Artificial Sequence
<220> FEATURE:
<223> OTHER INFORMATION: exemplary PET primer
<220> FEATURE:
<221> NAME/KEY: misc_feature
<222> LOCATION: (1)..(20)
<223> OTHER INFORMATION: PET tag portion of PET primer
<220> FEATURE:
<221> NAME/KEY: misc_feature
<222> LOCATION: (21)..(41)
<223> OTHER INFORMATION: sequence-specific primer portion of PET primer

<400> SEQUENCE: 11
aggcgcgatc acgcgcctgg actcataata actttacgga t                       41

<210> SEQ ID NO 12
<211> LENGTH: 44
<212> TYPE: DNA
<213> ORGANISM: Artificial Sequence
<220> FEATURE:
<223> OTHER INFORMATION: exemplary PET primer
<220> FEATURE:
<221> NAME/KEY: misc_feature
<222> LOCATION: (1)..(23)
<223> OTHER INFORMATION: PET tag portion of PET primer
<220> FEATURE:
<221> NAME/KEY: misc_feature
<222> LOCATION: (24)..(44)
<223> OTHER INFORMATION: sequence-specific primer portion of PET primer

<400> SEQUENCE: 12
aggcgcgatt cacgcgcctg gggactcata ataactttac ggat                    44

<210> SEQ ID NO 13
```

```
<211> LENGTH: 40
<212> TYPE: DNA
<213> ORGANISM: Artificial Sequence
<220> FEATURE:
<223> OTHER INFORMATION: Exemplary PET primer
<220> FEATURE:
<221> NAME/KEY: misc_feature
<222> LOCATION: (1)..(19)
<223> OTHER INFORMATION: PET tag portion of PET primer
<220> FEATURE:
<221> NAME/KEY: misc_feature
<222> LOCATION: (20)..(40)
<223> OTHER INFORMATION: sequence-specifc primer portion of PET primer

<400> SEQUENCE: 13
acccgcgata cgcgggtgga ctcataataa ctttacggat                          40

<210> SEQ ID NO 14
<211> LENGTH: 41
<212> TYPE: DNA
<213> ORGANISM: Artificial Sequence
<220> FEATURE:
<223> OTHER INFORMATION: Exemplary PET primer
<220> FEATURE:
<221> NAME/KEY: misc_feature
<222> LOCATION: (1)..(20)
<223> OTHER INFORMATION: PET tag portion of PET primer
<220> FEATURE:
<221> NAME/KEY: misc_feature
<222> LOCATION: (21)..(41)
<223> OTHER INFORMATION: sequence-specific primer portion of PET primer

<400> SEQUENCE: 14
acccgcgata ccgcgggtgg actcataata actttacgga t                        41

<210> SEQ ID NO 15
<211> LENGTH: 44
<212> TYPE: DNA
<213> ORGANISM: Artificial Sequence
<220> FEATURE:
<223> OTHER INFORMATION: exemplary PET primer
<220> FEATURE:
<221> NAME/KEY: misc_feature
<222> LOCATION: (1)..(23)
<223> OTHER INFORMATION: PET tag portion of PET primer
<220> FEATURE:
<221> NAME/KEY: misc_feature
<222> LOCATION: (24)..(44)
<223> OTHER INFORMATION: sequence-specifc primer portion of PET primer

<400> SEQUENCE: 15
acccgcgata accgcgggtg gggactcata ataactttac ggat                     44

<210> SEQ ID NO 16
<211> LENGTH: 38
<212> TYPE: DNA
<213> ORGANISM: Artificial Sequence
<220> FEATURE:
<223> OTHER INFORMATION: Exemplary PET primer
<220> FEATURE:
<221> NAME/KEY: misc_feature
<222> LOCATION: (1)..(17)
<223> OTHER INFORMATION: PET tag portion of PET primer
<220> FEATURE:
<221> NAME/KEY: misc_feature
<222> LOCATION: (18)..(38)
<223> OTHER INFORMATION: sequence-specific primer portion of PET primer

<400> SEQUENCE: 16
accgcgatac gcggtggact cataataact ttacggat                            38
```

```
<210> SEQ ID NO 17
<211> LENGTH: 39
<212> TYPE: DNA
<213> ORGANISM: Artificial Sequence
<220> FEATURE:
<223> OTHER INFORMATION: Exemplary PET primer
<220> FEATURE:
<221> NAME/KEY: misc_feature
<222> LOCATION: (1)..(18)
<223> OTHER INFORMATION: PET tag portion of PET primer
<220> FEATURE:
<221> NAME/KEY: misc_feature
<222> LOCATION: (19)..(39)
<223> OTHER INFORMATION: sequence-specific primer portion of PET primer

<400> SEQUENCE: 17
accgcgatca cgcggtggac tcataataac tttacggat                39

<210> SEQ ID NO 18
<211> LENGTH: 40
<212> TYPE: DNA
<213> ORGANISM: Artificial Sequence
<220> FEATURE:
<223> OTHER INFORMATION: Exemplary PET primer
<220> FEATURE:
<221> NAME/KEY: misc_feature
<222> LOCATION: (1)..(19)
<223> OTHER INFORMATION: PET tag portion of PET primer
<220> FEATURE:
<221> NAME/KEY: misc_feature
<222> LOCATION: (20)..(40)
<223> OTHER INFORMATION: sequence-specific primer portion of PET primer

<400> SEQUENCE: 18
accgcgattc acgcggtgga ctcataataa ctttacggat               40

<210> SEQ ID NO 19
<211> LENGTH: 36
<212> TYPE: DNA
<213> ORGANISM: Artificial Sequence
<220> FEATURE:
<223> OTHER INFORMATION: Exemplary PET primer
<220> FEATURE:
<221> NAME/KEY: misc_feature
<222> LOCATION: (1)..(15)
<223> OTHER INFORMATION: PET tag portion of PET primer
<220> FEATURE:
<221> NAME/KEY: misc_feature
<222> LOCATION: (16)..(36)
<223> OTHER INFORMATION: sequence-specific primer portion of PET primer

<400> SEQUENCE: 19
accgcatagc ggtggactca taataacttt acggat                   36

<210> SEQ ID NO 20
<211> LENGTH: 37
<212> TYPE: DNA
<213> ORGANISM: Artificial Sequence
<220> FEATURE:
<223> OTHER INFORMATION: Exemplary PET primer
<220> FEATURE:
<221> NAME/KEY: misc_feature
<222> LOCATION: (1)..(16)
<223> OTHER INFORMATION: PET tag portion of PET primer
<220> FEATURE:
<221> NAME/KEY: misc_feature
<222> LOCATION: (17)..(37)
<223> OTHER INFORMATION: sequence-specific primer portion of PET primer

<400> SEQUENCE: 20
accgcatcag cggtggactc ataataactt tacggat                  37
```

<210> SEQ ID NO 21
<211> LENGTH: 38
<212> TYPE: DNA
<213> ORGANISM: Artificial Sequence
<220> FEATURE:
<223> OTHER INFORMATION: Exemplary PET primer
<220> FEATURE:
<221> NAME/KEY: misc_feature
<222> LOCATION: (1)..(17)
<223> OTHER INFORMATION: PET tag portion of PET primer
<220> FEATURE:
<221> NAME/KEY: misc_feature
<222> LOCATION: (18)..(38)
<223> OTHER INFORMATION: sequence-specific primer portion of PET primer

<400> SEQUENCE: 21
accgcattca gcggtggact cataataact ttacggat        38

<210> SEQ ID NO 22
<211> LENGTH: 38
<212> TYPE: DNA
<213> ORGANISM: Artificial Sequence
<220> FEATURE:
<223> OTHER INFORMATION: Exemplary PET primer
<220> FEATURE:
<221> NAME/KEY: misc_feature
<222> LOCATION: (1)..(17)
<223> OTHER INFORMATION: PET tag portion of PET primer
<220> FEATURE:
<221> NAME/KEY: misc_feature
<222> LOCATION: (18)..(38)
<223> OTHER INFORMATION: sequence-specific primer portion of PET primer

<400> SEQUENCE: 22
aggcgcatag cgcctggact cataataact ttacggat        38

<210> SEQ ID NO 23
<211> LENGTH: 36
<212> TYPE: DNA
<213> ORGANISM: Artificial Sequence
<220> FEATURE:
<223> OTHER INFORMATION: Exemplary PET primer
<220> FEATURE:
<221> NAME/KEY: misc_feature
<222> LOCATION: (1)..(15)
<223> OTHER INFORMATION: PET tag portion of PET primer
<220> FEATURE:
<221> NAME/KEY: misc_feature
<222> LOCATION: (16)..(36)
<223> OTHER INFORMATION: sequence-specific primer portion of PET primer

<400> SEQUENCE: 23
aggcgatacg cctggactca taataacttt acggat        36

<210> SEQ ID NO 24
<211> LENGTH: 39
<212> TYPE: DNA
<213> ORGANISM: Artificial Sequence
<220> FEATURE:
<223> OTHER INFORMATION: Exemplary PET primer
<220> FEATURE:
<221> NAME/KEY: misc_feature
<222> LOCATION: (1)..(18)
<223> OTHER INFORMATION: PET tag portion of PET primer
<220> FEATURE:
<221> NAME/KEY: misc_feature
<222> LOCATION: (19)..(39)
<223> OTHER INFORMATION: sequence-specific primer portion of PET primer

<400> SEQUENCE: 24
aggcgcatca gcgcctggac tcataataac tttacggat        39

```
<210> SEQ ID NO 25
<211> LENGTH: 37
<212> TYPE: DNA
<213> ORGANISM: Artificial Sequence
<220> FEATURE:
<223> OTHER INFORMATION: Exemplary PET primer
<220> FEATURE:
<221> NAME/KEY: misc_feature
<222> LOCATION: (1)..(16)
<223> OTHER INFORMATION: PET tag portion of PET primer
<220> FEATURE:
<221> NAME/KEY: misc_feature
<222> LOCATION: (17)..(37)
<223> OTHER INFORMATION: sequence-specific primer portion of PET primer

<400> SEQUENCE: 25
aggcgatcac gcctggactc ataataactt tacggat                                37

<210> SEQ ID NO 26
<211> LENGTH: 40
<212> TYPE: DNA
<213> ORGANISM: Artificial Sequence
<220> FEATURE:
<223> OTHER INFORMATION: Exemplary PET primer
<220> FEATURE:
<221> NAME/KEY: misc_feature
<222> LOCATION: (1)..(19)
<223> OTHER INFORMATION: PET tag portion of PET primer
<220> FEATURE:
<221> NAME/KEY: misc_feature
<222> LOCATION: (20)..(40)
<223> OTHER INFORMATION: sequence-specific primer portion of PET primer

<400> SEQUENCE: 26
aggcgcattc agcgcctgga ctcataataa ctttacggat                             40

<210> SEQ ID NO 27
<211> LENGTH: 38
<212> TYPE: DNA
<213> ORGANISM: Artificial Sequence
<220> FEATURE:
<223> OTHER INFORMATION: Exemplary PET primer
<220> FEATURE:
<221> NAME/KEY: misc_feature
<222> LOCATION: (1)..(17)
<223> OTHER INFORMATION: PET tag portion of PET primer
<220> FEATURE:
<221> NAME/KEY: misc_feature
<222> LOCATION: (18)..(38)
<223> OTHER INFORMATION: sequence-specific primer portion of PET primer

<400> SEQUENCE: 27
aggcgattca cgcctggact cataataact ttacggat                               38

<210> SEQ ID NO 28
<211> LENGTH: 19
<212> TYPE: DNA
<213> ORGANISM: Artificial Sequence
<220> FEATURE:
<223> OTHER INFORMATION: Exemplary PET tag
<220> FEATURE:
<221> NAME/KEY: misc_feature
<222> LOCATION: (4)..(4)
<223> OTHER INFORMATION: n at position 4 is complementary to n at
      position 12
<220> FEATURE:
<221> NAME/KEY: misc_feature
<222> LOCATION: (5)..(5)
<223> OTHER INFORMATION: n at position 5 is complementary to n at
      position 11
<220> FEATURE:
```

```
<221> NAME/KEY: misc_feature
<222> LOCATION: (6)..(6)
<223> OTHER INFORMATION: n at position 6 is complementary to n at
      position 10
<220> FEATURE:
<221> NAME/KEY: misc_feature
<222> LOCATION: (10)..(10)
<223> OTHER INFORMATION: n at position 10 is complementary to n at
      position 6
<220> FEATURE:
<221> NAME/KEY: misc_feature
<222> LOCATION: (11)..(11)
<223> OTHER INFORMATION: n at position 11 is complementary to n at
      position 5
<220> FEATURE:
<221> NAME/KEY: misc_feature
<222> LOCATION: (12)..(12)
<223> OTHER INFORMATION: n at position 12 is complementary to n at
      position 4
<220> FEATURE:
<221> NAME/KEY: misc_feature
<222> LOCATION: (16)..(19)
<223> OTHER INFORMATION: G at positions 16 to 19 is two to four Gs.

<400> SEQUENCE: 28
aggnnnatan nncctgggg                                            19

<210> SEQ ID NO 29
<211> LENGTH: 17
<212> TYPE: DNA
<213> ORGANISM: Artificial Sequence
<220> FEATURE:
<223> OTHER INFORMATION: Exemplary PET tag
<220> FEATURE:
<221> NAME/KEY: misc_feature
<222> LOCATION: (16)..(17)
<223> OTHER INFORMATION: N is zero to two Gs.

<400> SEQUENCE: 29
aggcgcatag cgcctnn                                              17

<210> SEQ ID NO 30
<211> LENGTH: 34
<212> TYPE: DNA
<213> ORGANISM: Artificial Sequence
<220> FEATURE:
<223> OTHER INFORMATION: Exemplary PET primer
<220> FEATURE:
<221> NAME/KEY: misc_feature
<222> LOCATION: (1)..(15)
<223> OTHER INFORMATION: PET tag portion of PET primer
<220> FEATURE:
<221> NAME/KEY: misc_feature
<222> LOCATION: (1)..(1)
<223> OTHER INFORMATION: FAM label on the A
<220> FEATURE:
<221> NAME/KEY: misc_feature
<222> LOCATION: (16)..(34)
<223> OTHER INFORMATION: sequence-specific primer portion of PET primer

<400> SEQUENCE: 30
aggcgcatag cgcctatgac gggtaacggg gaat                           34

<210> SEQ ID NO 31
<211> LENGTH: 35
<212> TYPE: DNA
<213> ORGANISM: Artificial Sequence
<220> FEATURE:
<223> OTHER INFORMATION: exemplary PET primer
<220> FEATURE:
<221> NAME/KEY: misc_feature
<222> LOCATION: (1)..(16)
<223> OTHER INFORMATION: PET tag portion of PET primer
```

```
<220> FEATURE:
<221> NAME/KEY: misc_feature
<222> LOCATION: (1)..(1)
<223> OTHER INFORMATION: FAM label on the A
<220> FEATURE:
<221> NAME/KEY: misc_feature
<222> LOCATION: (17)..(35)
<223> OTHER INFORMATION: sequence-specific primer portion of PET primer

<400> SEQUENCE: 31
aggcgcatag cgcctgatga cgggtaacgg ggaat                               35

<210> SEQ ID NO 32
<211> LENGTH: 36
<212> TYPE: DNA
<213> ORGANISM: Artificial Sequence
<220> FEATURE:
<223> OTHER INFORMATION: Exemplary PET primer
<220> FEATURE:
<221> NAME/KEY: misc_feature
<222> LOCATION: (1)..(17)
<223> OTHER INFORMATION: PET tag portion of PET primer
<220> FEATURE:
<221> NAME/KEY: misc_feature
<222> LOCATION: (1)..(1)
<223> OTHER INFORMATION: FAM label on the A
<220> FEATURE:
<221> NAME/KEY: misc_feature
<222> LOCATION: (18)..(36)
<223> OTHER INFORMATION: sequence-specifc primer portion of PET primer

<400> SEQUENCE: 32
aggcgcatag cgcctggatg acgggtaacg gggaat                              36

<210> SEQ ID NO 33
<211> LENGTH: 23
<212> TYPE: DNA
<213> ORGANISM: Artificial Sequence
<220> FEATURE:
<223> OTHER INFORMATION: reverse sequence-specific primer

<400> SEQUENCE: 33
ccaattacaa aaccaaaaag tcc                                            23

<210> SEQ ID NO 34
<211> LENGTH: 36
<212> TYPE: DNA
<213> ORGANISM: Artificial Sequence
<220> FEATURE:
<223> OTHER INFORMATION: Exemplary PET primer
<220> FEATURE:
<221> NAME/KEY: misc_feature
<222> LOCATION: (1)..(17)
<223> OTHER INFORMATION: PET tag portion of PET primer
<220> FEATURE:
<221> NAME/KEY: misc_feature
<222> LOCATION: (1)..(1)
<223> OTHER INFORMATION: FAM label on the A
<220> FEATURE:
<221> NAME/KEY: misc_feature
<222> LOCATION: (18)..(36)
<223> OTHER INFORMATION: sequence-specific primer portion of PET primer

<400> SEQUENCE: 34
aggcggatac cgcctggatg acgggtaacg gggaat                              36

<210> SEQ ID NO 35
<211> LENGTH: 40
<212> TYPE: DNA
<213> ORGANISM: Artificial Sequence
<220> FEATURE:
```

```
<223> OTHER INFORMATION: Exemplary PET primer
<220> FEATURE:
<221> NAME/KEY: misc_feature
<222> LOCATION: (1)..(17)
<223> OTHER INFORMATION: PET tag portion of PET primer
<220> FEATURE:
<221> NAME/KEY: misc_feature
<222> LOCATION: (1)..(1)
<223> OTHER INFORMATION: HEX label on the A
<220> FEATURE:
<221> NAME/KEY: misc_feature
<222> LOCATION: (18)..(40)
<223> OTHER INFORMATION: sequence-specific primer portion of PET primer

<400> SEQUENCE: 35
aggcggatac cgcctggcca attacaaaac caaaaagtcc                              40

<210> SEQ ID NO 36
<211> LENGTH: 24
<212> TYPE: DNA
<213> ORGANISM: Artificial Sequence
<220> FEATURE:
<223> OTHER INFORMATION: Taqman probe
<220> FEATURE:
<221> NAME/KEY: misc_feature
<222> LOCATION: (1)..(1)
<223> OTHER INFORMATION: Quas670 label on the C
<220> FEATURE:
<221> NAME/KEY: misc_feature
<222> LOCATION: (24)..(24)
<223> OTHER INFORMATION: BHQ3 label on the G

<400> SEQUENCE: 36
cgcgcctgct gccttcctta gatg                                              24

<210> SEQ ID NO 37
<211> LENGTH: 36
<212> TYPE: DNA
<213> ORGANISM: Artificial Sequence
<220> FEATURE:
<223> OTHER INFORMATION: Exemplary PET primer
<220> FEATURE:
<221> NAME/KEY: misc_feature
<222> LOCATION: (1)..(17)
<223> OTHER INFORMATION: PET tag portion of PET primer
<220> FEATURE:
<221> NAME/KEY: misc_feature
<222> LOCATION: (1)..(1)
<223> OTHER INFORMATION: HEX label on the A
<220> FEATURE:
<221> NAME/KEY: misc_feature
<222> LOCATION: (18)..(36)
<223> OTHER INFORMATION: sequence-specific portion of PET primer

<400> SEQUENCE: 37
aggcggatac cgcctggatg acgggtaacg gggaat                                 36

<210> SEQ ID NO 38
<211> LENGTH: 40
<212> TYPE: DNA
<213> ORGANISM: Artificial Sequence
<220> FEATURE:
<223> OTHER INFORMATION: Exemplary PET primer
<220> FEATURE:
<221> NAME/KEY: misc_feature
<222> LOCATION: (1)..(17)
<223> OTHER INFORMATION: PET tag portion of PET primer
<220> FEATURE:
<221> NAME/KEY: misc_feature
<222> LOCATION: (1)..(1)
<223> OTHER INFORMATION: FAM label on the A
<220> FEATURE:
<221> NAME/KEY: misc_feature
```

-continued

```
<222> LOCATION: (18)..(40)
<223> OTHER INFORMATION: sequence-specific portion of PET primer

<400> SEQUENCE: 38
aggcggatac cgcctggcca attacaaaac caaaaagtcc                    40
```